Figure 1:
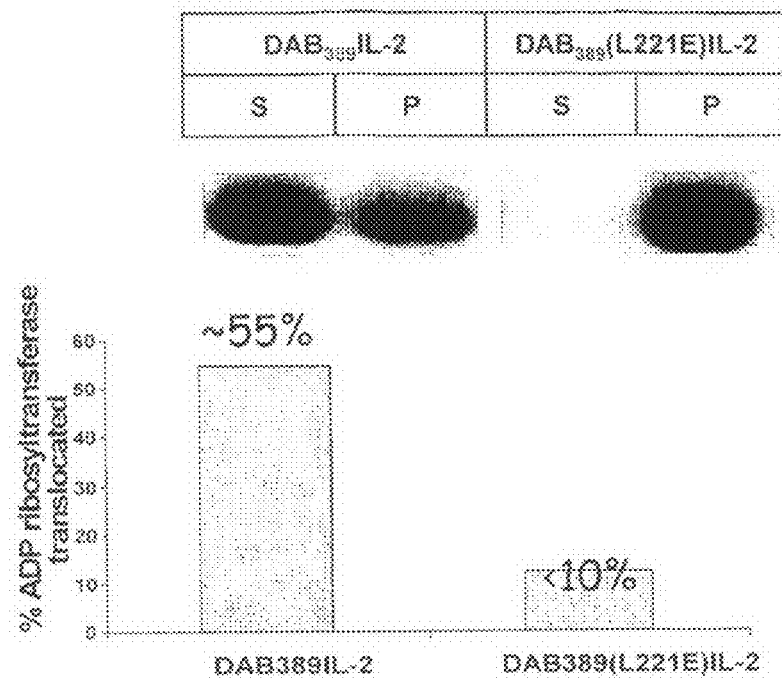
Figure 1:
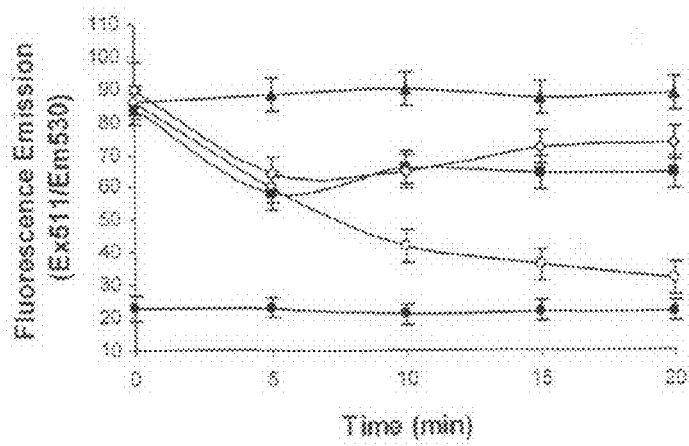

US008841253B2

(12) United States Patent
Murphy et al.

(10) Patent No.: US 8,841,253 B2
(45) Date of Patent: Sep. 23, 2014

(54) VIRAL/BACTERIAL TOXIN POLYPEPTIDES AND METHODS OF USING SAME

(75) Inventors: John R. Murphy, Boston, MA (US); Ryan Ratts, Boston, MA (US)

(73) Assignee: Boston Medical Center Corporation, Boston, MA (US)

( * ) Notice: Subject to any disclaimer, the term of this patent is extended or adjusted under 35 U.S.C. 154(b) by 798 days.

(21) Appl. No.: 12/065,066

(22) PCT Filed: Aug. 30, 2006

(86) PCT No.: PCT/US2006/033830

§ 371 (c)(1), (2), (4) Date: Feb. 27, 2008

(87) PCT Pub. No.: WO2007/126415
PCT Pub. Date: Nov. 8, 2007

(65) Prior Publication Data

US 2008/0306003 A1 Dec. 11, 2008

Related U.S. Application Data

(63) Continuation-in-part of application No. 11/214,997, filed on Aug. 30, 2005, now Pat. No. 7,517,667.

(51) Int. Cl.
*A61K 38/08* (2006.01)

(52) U.S. Cl.
USPC ................ 514/12; 514/2; 530/350; 530/328; 530/326; 530/324; 530/330

(58) Field of Classification Search
None
See application file for complete search history.

(56) References Cited

U.S. PATENT DOCUMENTS

| | | | | |
|---|---|---|---|---|
| 5,843,462 | A * | 12/1998 | Conti-Fine | 424/245.1 |
| 7,368,532 | B2 * | 5/2008 | Shone et al. | 530/350 |
| 2003/0220264 | A1 | 11/2003 | Rozema et al. | |

FOREIGN PATENT DOCUMENTS

WO WO 2005/014798 2/2005

OTHER PUBLICATIONS

Wells, Biochemistry, vol. 29, pp. 8509-8517, 1990.*
Seffernick et al. (J. Bacteriology, vol. 183, pp. 2405-2410, 2001).*
Andersson et al., "Protein Targeting to Endoplasmic Reticulum by Dilysine Signals Involves Direct Retention in Addition to Retrieval," *J. Biol. Chem.* 274:15080-15084, 1999.
International Preliminary Report on Patentability mailed Aug. 19, 2009 (PCT/US2006/033830).
International Search Report mailed Apr. 22, 2009 (PCT/US2006/033830).
Abrami et al., "Membrane Insertion of Anthrax Protective Antigen and Cytoplasmic Delivery of Lethal Factor Occur at Different Stages of the Endocytic Pathway," *J. Cell Biol.* 166:645-651, 2004.
Ariansen et al., "Membrane Translocation of Diphtheria Toxin A-Fragment: Role of Carboxy-Terminal Region," *Biochemistry.* 32:83-90, 1993.
Arora et al., "Fusions of Anthrax Toxin Lethal Factor with Shiga Toxin and Diphtheria Toxin Enzymatic Domains Are Toxic to Mammalian Cells," *Infect. Immun.* 62:4955-4961, 1994.

Arora et al., "Residues 1-254 of Anthrax Toxin Lethal Factor are Sufficient to Cause Cellular Uptake of Fused Polypeptides," *J. Biol. Chem.* 268:3334-3341, 1993.

Bacha et al., "Interleukin 2 Receptor-Targeted Cytotoxicity," *J. Exp. Med.* 167:612-622, 1988.

Bennett et al., "Domain Swapping: Entangling Alliances Between Proteins," *Proc. Natl. Acad. Sci. USA* 91:3127-3131, 1994.

Bharti et al., "Identification of a Nucleolin Binding Site in Human Topoisomerase I," *J. Biol. Chem.* 271:1993-1997, 1996.

Binz et al., "$Arg^{362}$ and $Tyr^{365}$ of the Botulinum Neurotoxin Type A Light Chain Are Involved in Transition State Stabilization," *Biochem.* 41:1717-1723, 2002.

Boquet et al., "Binding of Triton X-100 to Diphtheria Toxin, Crossreacting Material 45, and their Fragments," *Proc. Natl. Acad. Sci. USA* 73:4449-4453, 1976.

Chadwick et al., "Cytotoxicity of a Recombinant Diphtheria Toxin-Granulocyte Colony-Stimulating Factor Fusion Protein on Human Leukemic Blast Cells," *Leukemia and Lymphoma* 11:249-262, 1993.

Chung et al., "The Mechanism of ADP-Ribosylation of Elongation Factor 2 Catalyzed by Fragment A from Diphtheria Toxin," *Biochem. Biophys. Acta.* 483:248-257, 1977.

Donovan et al., "Diphtheria Toxin Forms Transmembrane Channels in Planar Lipid Bilayers," *Proc. Natl. Acad. Sci., USA* 78:172-176, 1981.

Duden et al., "β-COP, A 110 kd Protein Associated with Non-Clathrin-Coated Vesicles and the Golgi Complex, Shows Homology to β-Adaptin," *Cell* 64:649-665, 1991.

Duprez et al., "Receptor-Mediated Endocytosis of Interleukin 2 in a Human Tumor T Cell Line," *J. Biol. Chem.* 261:15450-15454, 1986.

Haug et al., "The Host Cell Chaperone Hsp90 is Necessary for Cytotoxic Action of the Binary Iota-Like Toxins," *Infect. Immun.* 72:3066-3068, 2004.

Hu et al., "The Effects of Helix Breaking Mutations in the Diphtheria Toxin Transmembrane Domain Helix Layers of the Fusion Toxin $DAB_{389}$IL-2," *Protein Eng.* 11:811-817, 1998.

(Continued)

*Primary Examiner* — Hope Robinson

(74) *Attorney, Agent, or Firm* — Clark & Elbing LLP; Todd Armstrong

(57) ABSTRACT

The invention features methods for identifying compounds that inhibit cell death, and methods for identifying compounds that promote cell death, by blocking or accelerating, respectively, the translocation of the catalytic domain of toxins or transcription factors through the endosomal membrane into the cytosol of a cell. Also featured are methods for inhibiting cell death that include the administration of polypeptides that include a toxin consensus sequence recognized by one or more components of the cytosolic translocation factor complex.

12 Claims, 4 Drawing Sheets

(56) References Cited

OTHER PUBLICATIONS

Jackson et al., "The KDEL Retrieval System is Exploited by *Pseudomonas* Exotoxin A, but not by Shiga-Like Toxin-1, During Retrograde Transport from the Golgi Complex to the Endoplasmic Reticulum," *J. Cell Sci.* 112:467-475, 1999.

Jean et al., "Diphtheria Toxin Receptor-Binding Domain Substitution with Interleukin 6: Genetic Construction and Interleukin 6 Receptor-Specific Action of a Diphtheria Toxin-Related Interleukin 6 Fusion Protein," *Protein Eng.* 4:989-994, 1991.

Kagan et al., "Diphtheria Toxin Fragment Forms Large Pores in Phospholipid Bilayer Membranes," *Proc. Natl. Acad. Sci., USA* 78:4950-4954, 1981.

Kelley et al., "Interleukin 2-Diphtheria Toxin Fusion Protein Can Abolish Cell-Mediated Immunity In Vivo," *Proc. Natl. Acad. Sci. USA* 85:3980-3984, 1988.

Kiyokawa et al., "Cytotoxicity of Interleukin 2-Toxin Toward Lymphocytes from Patients with Adult T-Cell Leukemia," *Cancer Res.* 49:4042-4046, 1989.

Kiyokawa et al., "Protein Engineering of DAB-IL-2 Fusion Toxins to Increase Biologic Potency," *Ann. NY Acad. Sci.* 636:331-339, 1991.

Kiyokawa et al., "Protein Engineering of Diphtheria-Toxin-Related Interleukin-2 Fusion Toxins to Increase Cytotoxic Potency for High-Affinity IL-2-Receptor-Bearing Target Cells," *Protein Eng.* 4:463-468, 1991.

Kochi et al., "DNA Fragmentation and Cytolysis in U937 Cells Treated with Diphtheria Toxin or Other Inhibitors of Protein Synthesis," *Exp. Cell. Res.* 208:296-302, 1993.

Lacy et al., "Mapping the Anthrax Protective Antigen Binding Site on the Lethal and Edema Factors," *J. Biol. Chem.* 277:3006-3010, 2002.

Lemichez et al., "Membrane Translocation of Diphtheria Toxin Fragment A Exploits Early to Late Endosome Trafficking Machinery," *Mol. Microbiol.* 23:445-457, 1997.

Liger et al., "The Diphtheria Toxin Transmembrane Domain as a pH Sensitive Membrane Anchor for Human Interleukin-2 and Murine Interleukin-3," *Protein Eng.* 11:1111-1120, 1998.

Lord et al., "Toxin Entry: Retrograde Transport Through the Secretory Pathway," *J. Cell Biol.* 140:733-736, 1998.
Love et al., "*Corynebacterium diphtheriae:* Iron-Mediated Activation of DtxR and Regulation of Diphtheria Toxin Expression," *Gram-Positive Pathogens,* 573-582, 2000.
McMahon et al., "COP and Clathrin-Coated Vesicle Budding: Different Pathways, Common Approaches," *Curr. Opin. Cell Biol.* 16:379-391, 2004.

Mitamura et al., "The 27-kD Diphtheria Toxin Receptor-Associated Protein (DRAP27) From Vero Cells is the Monkey Homologue of Human CD9 Antigen: Expression of DRAP27 Elevates the Number of Diphtheria Toxin Receptors on Toxin-Sensitive Cells," *J. Cell Biol.* 118:1389-1399, 1992.

Moya et al., "Inhibition of Coated Pit Formation in $Hep_2$ Cells Blocks the Cytotoxicity of Diphtheria toxin but not that of Ricin Toxin," *J. Cell. Biol.* 101:548-559, 1985.

Murphy et al., "Cell Receptor Specific Targeted Toxins: Genetic Construction and Characterization of an Interleukin 2 Diphtheria Toxin-Related Fusion Protein," *J. Recept. Res.* 8:467-480, 1988.

Murphy, "Diphtheria-Related Peptide Hormone Gene Fusions: A Molecular Genetic Approach to Chimeric Toxin Development," *Cancer Treat. Res.* 37:123-140, 1988.

Murphy et al., "Genetic Assembly and Selective Toxicity of Diphtheria-Toxin-Related Polypeptide Hormone Fusion Proteins," *Biochem. Soc. Symp.* 53:9-23, 1987.

Murphy et al., "Interleukin 2 Toxin: A Step Toward Selective Immunomodulation," *Am. J. Kidney Dis.* 11:159-162, 1988.

Murphy et al., "Protein Engineering of Diphtheria Toxin," *Targeted Diagn. Ther.* 7:365-382, 1992.

Murphy et al., "Targeting Diphtheria Toxin to Growth Factor Receptors," *Semin. Cancer Biol.* 6:259-267, 1995.

O'Keefe et al., "pH-Dependent Insertion of Proteins into Membranes: B-Chain Mutation of Diphtheria Toxin that Inhibits Membrane Translocation, Glu-349→Lys," *Proc. Natl. Acad. Sci. USA* 89:6202-6206, 1992.

Oh et al., "Translocation of the Catalytic Domain of Diphtheria Toxin Across Planar Phospholipid Bilayers by its Own T Domain," *Proc. Natl. Acad. Sci. USA* 96:8467-8470, 1999.
Perentesis et al., "Expression of Diphtheria Toxin Fragment A and Hormone-Toxin Fusion Proteins in Toxin-Resistant Yeast Mutants," *Proc. Natl. Acad. Sci. USA* 85:8386-8390, 1988.
Ratts et al., "Diphtheria Toxin-Structure, Function, and its Clinical Applications," *Chimeric Toxins* 14-36, 2002.
Ratts et al., "The Cytosolic Entry of Diphtheria Toxin Catalytic Domain Requires a Host Cell Cytosolic Translocation Factor Complex," *J. Cell. Biol.* 160:1139-1150, 2003.
Rebbe et al., "Nucleotide Sequence and Regulation of a Human 90-kDa Heat Shock Protein Gene," *J. Biol. Chem.* 264:15006-15011, 1989.
Ren et al., "Interaction of Diphtheria Toxin T Domain with Molten Globule-Like Proteins and its Implications for Translocation," *Science* 284:955-957, 1999.
Sandvig et al., "Pathways Followed by Protein Toxins Into Cells," *Int. J. Med. Microbiol.* 293:483-490, 2004.
Tsuneoka et al., "Evidence for Involvement of Furin in Cleavage and Activation of Diphtheria Toxin," *J. Biol. Chem.* 268:26461-26465, 1993.
Uchida, "Diphtheria Toxin and Related Proteins," *J. Biol. Chem.* 248:3838-3844, 1973.
VanderSpek et al., "An Intact Transmembrane Helix 9 is Essential for the Efficient Delivery of the Diphtheria Toxin Catalytic Domain to the Cytosol of Target Cells," *J. Biol. Chem.* 269:21455-21459, 1994.
VanderSpek et al., "$DAB_{389}$ Interleukin-2 Receptor Binding Domain Mutations," *J. Biol. Chem.* 271:12145-12149, 1996.
VanderSpek et al., "Epitope Tagging of $DAB_{389}$IL-2: New Insights into C-Domain Delivery to the Cytosol of Target Cells," *Leukemia* 8:S144-S148, 1994.
VanderSpek et al., "Genetic Construction and Characterization of the Diphtheria Toxin-Related Interleukin 15 Fusion Protein $DAB_{389}$ sIL-15," *Protein Eng.* 8:1317-1321, 1995.
VanderSpek et al., "Maintenance of the Hydrophobic Face of the Diphtheria Toxin Amphipathic Transmembrane Helix 1 is Essential for the Efficient Delivery of the Catalytic Domain to the Cytosol of Target Cells," *Protein Eng.* 7:985-989, 1994.
VanderSpek et al., "Structure/Function Analysis of the Transmembrane Domain of $DAB_{389}$-Interleukin-2, an Interleukin-2 Receptor-Targeted Fusion Toxin," *J. Biol. Chem.* 268:12077-12082, 1993.
Walz et al., "Sequential Effects of Interleukin 2-Diphtheria Toxin Fusion Protein on T-Cell Activation," *Proc. Natl. Acad. Sci. USA* 86:9485-9488, 1989.
Waters et al., "Interleukin 2 Receptor-Targeted Cytotoxicity. Receptor Binding Requirements for Entry of a Diphtheria Toxin-Related Interleukin 2 Fusion Protein into Cells," *Eur. J. Immunol.* 20:785-791, 1990.
Wesche et al., "Characterization of Membrane Translocation by Anthrax Protective Antigen," *Biochemistry* 37:15737-15746, 1998.
Williams et al., "Cellular Processing of the Interleukin-2 Fusion Toxin $DAB_{486}$-IL-2 and Efficient Delivery of Diphtheria Fragment A to the Cytosol of Target Cells Requires $Arg^{194}$," *J. Biol. Chem.* 265:20673-20677, 1990.
Williams et al., "Structure/Function Analysis of Interleukin-2-Toxin ($DAB_{486}$-IL-2," J. *Biol. Chem.* 265:11885-11889, 1990.
Zhang et al., "Evidence that Translocation of Anthrax Toxin's Lethal Factor is Initiated by Entry of its N Terminus into the Protective Antigen Channel," *Proc. Natl. Acad. Sci. USA* 101:16756-16761, 2004.

* cited by examiner (A)

(B)

(A)

(B)

SEQUENCE LISTING

```
<160> NUMBER OF SEQ ID NOS: 47

<210> SEQ ID NO 1
<211> LENGTH: 20
<212> TYPE: PRT
<213> ORGANISM: Corynebacterium diptheriae

<400> SEQUENCE: 1

Arg Asp Lys Thr Lys Thr Lys Ile Glu Ser Leu Lys Glu His Gly Pro
1               5                   10                  15

Ile Lys Asn Ser
            20

<210> SEQ ID NO 2
<211> LENGTH: 10
<212> TYPE: PRT
<213> ORGANISM: Artificial Sequence
<220> FEATURE:
<223> OTHER INFORMATION: synthetic

<400> SEQUENCE: 2

Thr Gln Ile Glu Asn Leu Lys Glu Lys Gly
1               5                   10

<210> SEQ ID NO 3
<211> LENGTH: 35
<212> TYPE: PRT
<213> ORGANISM: Corynebacterium diptheriae

<400> SEQUENCE: 3

Lys Thr Lys Thr Lys Ile Glu Ser Leu Lys Glu His Gly Pro Ile Lys
1               5                   10                  15

Asn Lys Met Ser Glu Ser Pro Asn Lys Thr Val Ser Glu Glu Lys Ala
            20                  25                  30

Lys Gln Tyr
        35

<210> SEQ ID NO 4
<211> LENGTH: 56
<212> TYPE: PRT
<213> ORGANISM: Corynebacterium diptheriae

<400> SEQUENCE: 4

Cys Ile Asn Leu Asp Trp Asp Val Ile Arg Asp Lys Thr Lys Thr Lys
1               5                   10                  15

Ile Glu Ser Leu Lys Glu His Gly Pro Ile Lys Asn Lys Met Ser Glu
            20                  25                  30

Ser Pro Asn Lys Thr Val Ser Glu Glu Lys Ala Lys Gln Tyr Leu Glu
            35                  40                  45
```

```
Glu Phe His Gln Thr Ala Leu Glu
    50                  55

<210> SEQ ID NO 5
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 5

Lys Xaa Lys Xaa Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: synthetic

<400> SEQUENCE: 6

Thr Gln Ile Glu Asn Leu Lys Glu Lys Gly
1               5                   10

<210> SEQ ID NO 7
<211> LENGTH: 10
<212> TYPE: PRT
<213> ORGANISM: Corynebacterium diptheriae

<400> SEQUENCE: 7

Thr Lys Ile Glu Ser Leu Lys Glu His Gly
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Arg Asp Lys Thr Lys Thr Gln Ile Glu Asn Leu Lys Glu Lys Gly
1               5                   10                  15

<210> SEQ ID NO 9
<211> LENGTH: 15
<212> TYPE: PRT
<213> ORGANISM: Corynebacterium diptheriae

<400> SEQUENCE: 9

Arg Asp Lys Thr Lys Thr Lys Ile Glu Ser Leu Lys Glu His Gly
1               5                   10                  15

<210> SEQ ID NO 10
<211> LENGTH: 17
<212> TYPE: PRT
<213> ORGANISM: Artificial Sequence
<220>

<223> OTHER INFORMATION: synthetic

<400> SEQUENCE: 10

Thr Gln Ile Glu Asn Leu Lys Glu Lys Gly Pro Ile Lys Asn Lys Met
1               5                   10                  15

Ser

<210> SEQ ID NO 11
<211> LENGTH: 17
<212> TYPE: PRT
<213> ORGANISM: Corynebacterium diptheriae

<400> SEQUENCE: 11

Thr Lys Ile Glu Ser Leu Lys Glu His Gly Pro Ile Lys Asn Lys Met
1               5                   10                  15

Ser

<210> SEQ ID NO 12
<211> LENGTH: 22
<212> TYPE: PRT
<213> ORGANISM: Artificial Sequence
<220> FEATURE:
<223> OTHER INFORMATION: synthetic

<400> SEQUENCE: 12

Arg Asp Lys Thr Lys Thr Gln Ile Glu Asn Leu Lys Glu Lys Gly Pro
1

```
Thr Lys Thr Gln Ile Glu Gln Leu Lys Glu Lys Gly
1               5                   10
```

<210> SEQ ID NO 16
<211> LENGTH: 20
<212> TYPE: PRT
<213> ORGANISM: Artificial Sequence
<220> FEATURE:
<223> OTHER INFORMATION: synthetic

<400> SEQUENCE: 16

```
Arg Asp Lys Thr Lys Thr Gln Ile Glu Gln Leu Lys Glu Lys Gly Pro
1               5                   10                  15

Ile Lys Asn Lys
            20
```

<210> SEQ ID NO 17
<211> LENGTH: 20
<212> TYPE: PRT
<213> ORGANISM: Artificial Sequence
<220> FEATURE:
<223> OTHER INFORMATION: synthetic

<400> SEQUENCE: 17

```
Asp Trp Asp Val Ile Arg Asp Lys Thr Lys Thr Gln Ile Glu Gln Leu
1               5                   10                  15

Lys Glu Lys Gly
            20
```

<210> SEQ ID NO 18
<211> LENGTH: 22
<212> TYPE: PRT
<213> ORGANISM: Artificial Sequence
<220> FEATURE:
<223> OTHER INFORMATION: synthetic

<400> SEQUENCE: 18

```
Arg Asp Lys Thr Lys Thr Lys Thr Gln Ile Glu Gln Leu Lys Glu Lys
1               5                   10                  15

Gly Pro Ile Lys Asn Lys
            20
```

<210> SEQ ID NO 19
<211> LENGTH: 16
<212> TYPE: PRT
<213> ORGANISM: Bacillus anthracis

<400> SEQUENCE: 19

```
Glu Lys Asn Lys Thr Glu Lys Glu Lys Phe Lys Asp Ser Ile Asn Asn
1               5                   10                  15
```

<210> SEQ ID NO 20
<211> LENGTH: 16
<212> TYPE: PRT
<213> ORGANISM: Bacillus anthracis

<400> SEQUENCE: 20

```
Lys Leu Asp His Leu Arg Ile Glu Glu Leu Lys Glu Asn Gly Ile Ile
1               5                   10                  15
```

<210> SEQ ID NO 21
<211> LENGTH: 16
<212> TYPE: PRT
<213> ORGANISM: Bacillus anthracis

```
<400> SEQUENCE: 21

Glu Arg Asn Lys Thr Gln Glu Glu His Leu Lys Glu Ile Met Lys His
1               5                   10                  15

<210> SEQ ID NO 22
<211> LENGTH: 16
<212> TYPE: PRT
<213> ORGANISM: Clostridium botulinum

<400> SEQUENCE: 22

Ala Lys Val Asn Thr Gln Ile Asp Leu Ile Arg Lys Lys Met Lys Glu
1               5                   10                  15

<210> SEQ ID NO 23
<211> LENGTH: 16
<212> TYPE: PRT
<213> ORGANISM: Clostridium botulinum

<400> SEQUENCE: 23

Gly Thr Leu Ile Gly Gln Val Asp Arg Leu Lys Asp Lys Val Asn Asn
1               5                   10                  15

<210> SEQ ID NO 24
<211> LENGTH: 16
<212> TYPE: PRT
<213> ORGANISM: Clostridium botulinum

<400> SEQUENCE: 24

Glu Asn Ile Lys Ser Gln Val Glu Asn Leu Lys Asn Ser Leu Asp Val
1               5                   10                  15

<210> SEQ ID NO 25
<211> LENGTH: 16
<212> TYPE: PRT
<213> ORGANISM: Clostridium botulinum

<400> SEQUENCE: 25

Glu Asn Ile Lys Ser Gln Val Glu Asn Leu Lys Asn Ser Leu Asp Val
1               5                   10                  15

<210> SEQ ID NO 26
<211> LENGTH: 16
<212> TYPE: PRT
<213> ORGANISM: Corynebacterium diphtheriae

<400> SEQUENCE: 26

Asp Lys Thr Lys Thr Lys Ile Glu Ser Leu Lys Glu His Gly Pro Ile
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: synthetic

<400> SEQUENCE: 27

Thr Gln Ile Glu Asn Leu Lys Glu Asn Gly
1               5                   10

<210> SEQ ID NO 28
<211> LENGTH: 27
<212> TYPE: DNA
<213> ORGANISM: Artificial Sequence
<220> FEATURE:
```

<223> OTHER INFORMATION: synthetic

<400> SEQUENCE: 28
cgcggatccc ccttcgctga ggggagt                                   27

<210> SEQ ID NO 29
<211> LENGTH: 27
<212> TYPE: DNA
<213> ORGANISM: Artificial Sequence
<220> FEATURE:
<223> OTHER INFORMATION: synthetic

<400> SEQUENCE: 29
ccgctcgagc gggttggtac cagtaac                                   27

<210> SEQ ID NO 30
<211> LENGTH: 50
<212> TYPE: DNA
<213> ORGANISM: Artificial Sequence
<220> FEATURE:
<223> OTHER INFORMATION: synthetic

<400> SEQUENCE: 30
tcccacacta agatcgaatc tctgatcaag agatcagaga ttcgatctta          50

<210> SEQ ID NO 31
<211> LENGTH: 49
<212> TYPE: DNA
<213> ORGANISM: Artificial Sequence
<220> FEATURE:
<223> OTHER INFORMATION: synthetic

<400> SEQUENCE: 31
attctagctt agagactagt tctctagtct ctaagctaga atcaaaaac           49

<210> SEQ ID NO 32
<211> LENGTH: 42
<212> TYPE: RNA
<213> ORGANISM: Artificial Sequence
<220> FEATURE:
<223> OTHER INFORMATION: synthetic

<400> SEQUENCE: 32
uaagaucgaa ucucugauca agagaucaga gauucgaucu ua                 42

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
ccatgagtga taaaactaaa                                           20

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
attaggaaag gacagtggga                                           20

<210> SEQ ID NO 35
<211> LENGTH: 19
<212> TYPE: PRT
<213> ORGANISM: Artificial Sequence
<220> FEATURE:
<223> OTHER INFORMATION: synthetic

<400> SEQUENCE: 35

Ala Glu Asn Ser Asp Lys His Arg Ile Met Gln Val Phe His Arg Thr
1               5                   10                  15

Leu Asn Gln

<210> SEQ ID NO 36
<211> LENGTH: 6249
<212> TYPE: DNA
<213> ORGANISM: Artificial Sequence
<220> FEATURE:
<223> OTHER INFORMATION: Plasmid pP1

<400> SEQUENCE: 36

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caaactccgc ccattgacgc aaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctat     960
accatgcgtg ataaaactaa aactaagatc gaatctctga agaacacgg tccgatcaaa    1020
aacaaatagt ctagagggcc cgtttaaacc cgctgatcag cctcgactgt gccttctagt    1080
tgccagccat ctgttgtttg cccctccccc gtgccttcct tgaccctgga aggtgccact    1140
cccactgtcc tttcctaata aaatgaggaa attgcatcgc attgtctgag taggtgtcat    1200
tctattctgg ggggtggggt ggggcaggac agcaagggggg aggattggga agacaatagc    1260
agctttgcaa agatggataa agttttaaac agagaggaat ctttgcagct aatggacctt    1320
ctaggtcttg aaaggagtgc ctcgtgaggc tccggtgccc gtcagtgggc agagcgcaca    1380
tcgcccacag tccccgagaa gttgggggga gggtcggca attgaaccgg tgcctagaga    1440
aggtggcgcg gggtaaactg ggaaagtgat gtcgtgtact ggctccgcct ttttcccgag    1500
ggtgggggag aaccgtatat aagtgcagta gtcgccgtga acgttctttt tcgcaacggg    1560
tttgccgcca gaacacaggt aagtgccgtg tgtggttccc gcgggcctgg cctctttacg    1620
ggttatggcc cttgcgtgcc ttgaattact tccacctggc tgcagtacgt gattcttgat    1680
```

```
cccgagcttc gggttggaag tgggtgggag agttcgaggc cttgcgctta aggagcccct    1740
tcgcctcgtg cttgagttga ggcctggcct gggcgctggg gccgccgcgt gcgaatctgg    1800
tggcaccttc gcgcctgtct cgctgctttc gataagtctc tagccattta aaattttga    1860 tgacctgctg cgacgctttt tttctggcaa gatagtcttg taaatgcggg ccaagatctg    1920
cacactggta tttcggtttt tggggccgcg ggcggcgacg gggcccgtgc gtcccagcgc    1980
acatgttcgg cgaggcgggg cctgcgacg cggccaccga gaatcggacg ggggtagtct    2040
caagctggcc ggcctgctct ggtgcctggc ctcgcgccgc cgtgtatcgc cccgccctgg    2100
gcggcaaggc tgggcccggtc ggcaccagtt gcgtgagcgg aaagatggcc gcttcccggc    2160
cctgctgcag ggagctcaaa atggaggacg cggcgctcgg gagagcgggc gggtgagtca    2220
cccacacaaa ggaaaagggc ctttccgtcc tcagccgtcg cttcatgtga ctccacggag    2280
taccgggcgc cgtccaggca cctcgattag ttctcgagct tttggagtac gtcgtcttta    2340
ggttgggggg aggggttta tgcgatgag tttccccaca ctgagtgggt ggagactgaa    2400
gttaggccag cttggcactt gatgtaattc tccttggaat ttgcccttt tgagtttgga    2460 tcttggttca ttctcaagcc tcagacagtg gttcaaagtt tttttcttcc atttcaggtg    2520
tcgtgaggaa ttagcttggt actaatacga ctcactatag ggagacccaa gctggctagg    2580
taagctccta ggcttttgca aaagctccc gggagcttgt atatccattt tcggatctga    2640
tcagcacgtg ttgacaatta atcatcggca tagtatatcg gcatagtata atacgacaag    2700
gtgaggaact aaaccatggc tagcaaagga gaagaacttt tcactggagt tgtcccaatt    2760
cttgttgaat tagatggtga tgttaatggg cacaaatttt ctgtcagtgg agagggtgaa    2820
ggtgatgcta catacggaaa gcttaccctt aaatttattt gcactactgg aaaactacct    2880
gttccatggc caacacttgt cactactttc tcttatggtg ttcaatgctt ttcccgttat    2940
ccggatcata tgaaacggca tgacttttc aagagtgcca tgcccgaagg ttatgtacag    3000
gaacgcacta tatctttcaa agatgacggg aactacaaga cgcgtgctga agtcaagttt    3060
gaaggtgata cccttgttaa tcgtatcgag ttaaaggta ttgattttaa agaagatgga    3120
aacattctcg gacacaaact cgagtacaac tataactcac acaatgtata catcacggca    3180
gacaaacaaa agaatggaat caaagctaac ttcaaaattc gccacaacat tgaagatgga    3240
tccgttcaac tagcagacca ttatcaacaa atactccaa ttggcgatgg ccctgtcctt    3300
ttaccagaca accattacct gtcgacacaa tctgcccttt cgaaagatcc caacgaaaag    3360
cgtgaccaca tggtccttct tgagtttgta actgctgctg ggattacaca tggcatggat    3420
gccaagttga ccagtgccgt tccggtgctc accgcgcgcg acgtcgccgg agcggtcgag    3480
ttctggaccg accggctcgg gttctcccgg gacttcgtgg aggacgactt cgccggtgtg    3540
gtccgggacg acgtgaccct gttcatcagc gcggtccagg accaggtggt gccggacaac    3600
accctggcct gggtgtgggt gcgcggcctg gacgagctgt acgccgagtg gtcggaggtc    3660
gtgtccacga acttccggga cgcctccggg ccggccatga ccgagatcgg cgagcagccg    3720
tgggggcggg agttcgccct gcgcgacccg gccggcaact gcgtgcactt cgtggccgag    3780
gagcaggact gacacgtgct acgagatttc gattccaccg ccgccttcta tgaaaggttg    3840
ggcttcggaa tcgttttccg ggacgccggc tggatgatcc tccagcgcgg ggatctcatg    3900
ctggagttct tcgcccaccc caacttgttt attgcagctt ataatggtta caaataaagc    3960
aatagcatca caaatttcac aaataaagca ttttttttcac tgcattctag ttgtggtttg    4020
```

| | | | | | |
|---|---|---|---|---|---|
| tccaaactca | tcaatgtatc | ttatcatgtc | tgtataccgt | cgacctctag | ctagagcttg | 4080 |
| gcgtaatcat | ggtctatagct | gtttcctgtg | tgaaattgtt | atccgctcac | aattccacac | 4140 |
| aacatacgag | ccggaagcat | aaagtgtaaa | gcctggggtg | cctaatgagt | gagctaactc | 4200 |
| acattaattg | cgttgcgctc | actgcccgct | ttccagtcgg | gaaacctgtc | gtgccagctg | 4260 |
| cattaatgaa | tcggccaacg | cgcggggaga | ggcggtttgc | gtattgggcg | ctcttccgct | 4320 |
| tcctcgctca | ctgactcgct | gcgctcggtc | gttcggctgc | ggcgagcggt | atcagctcac | 4380 |
| tcaaaggcgg | taatacggtt | atccacagaa | tcaggggata | acgcaggaaa | gaacatgtga | 4440 |
| gcaaaaggcc | agcaaaaggc | caggaaccgt | aaaaaggccg | cgttgctggc | gtttttccat | 4500 |
| aggctccgcc | cccctgacga | gcatcacaaa | aatcgacgct | caagtcagag | gtggcgaaac | 4560 |
| ccgacaggac | tataaagata | ccaggcgttt | ccccctggaa | gctccctcgt | gcgctctcct | 4620 |
| gttccgaccc | tgccgcttac | cggatacctg | tccgcctttc | tcccttcggg | aagcgtggcg | 4680 |
| ctttctcaat | gctcacgctg | taggtatctc | agttcggtgt | aggtcgttcg | ctccaagctg | 4740 |
| ggctgtgtgc | acgaaccccc | cgttcagccc | gaccgctgcg | ccttatccgg | taactatcgt | 4800 |
| cttgagtcca | acccggtaag | acacgactta | tcgccactgg | cagcagccac | tggtaacagg | 4860 |
| attagcagag | cgaggtatgt | aggcggtgct | acagagttct | tgaagtggtg | gcctaactac | 4920 |
| ggctacacta | gaaggacagt | atttggtatc | tgcgctctgc | tgaagccagt | taccttcgga | 4980 |
| aaaagagttg | gtagctcttg | atccggcaaa | caaaccaccg | ctggtagcgg | tggtttttt | 5040 |
| gtttgcaagc | agcagattac | gcgcagaaaa | aaaggatctc | aagaagatcc | tttgatcttt | 5100 |
| tctacggggt | ctgacgctca | gtggaacgaa | aactcacgtt | aagggatttt | ggtcatgaga | 5160 |
| ttatcaaaaa | ggatcttcac | ctagatcctt | ttaaattaaa | aatgaagttt | taaatcaatc | 5220 |
| taagtatat | atgagtaaac | ttggtctgac | agttaccaat | gcttaatcag | tgaggcacct | 5280 |
| atctcagcga | tctgtctatt | tcgttcatcc | atagttgcct | gactccccgt | cgtgtagata | 5340 |
| actacgatac | gggagggctt | accatctggc | cccagtgctg | caatgatacc | gcgagaccca | 5400 |
| cgctcaccgg | ctccagattt | atcagcaata | aaccagccag | ccggaagggc | cgagcgcaga | 5460 |
| agtggtcctg | caactttatc | cgcctccatc | cagtctatta | attgttgccg | ggaagctaga | 5520 |
| gtaagtagtt | cgccagttaa | tagtttgcgc | aacgttgttg | ccattgctac | aggcatcgtg | 5580 |
| gtgtcacgct | cgtcgtttgg | tatggcttca | ttcagctccg | gttcccaacg | atcaaggcga | 5640 |
| gttacatgat | cccccatgtt | gtgcaaaaaa | gcggttagct | ccttcggtcc | tccgatcgtt | 5700 |
| gtcagaagta | agttggccgc | agtgttatca | ctcatggtta | tggcagcact | gcataattct | 5760 |
| cttactgtca | tgccatccgt | aagatgcttt | tctgtgactg | gtgagtactc | aaccaagtca | 5820 |
| ttctgagaat | agtgtatgcg | gcgaccgagt | tgctcttgcc | cggcgtcaat | acgggataat | 5880 |
| accgcgccac | atagcagaac | tttaaaagtg | ctcatcattg | gaaaacgttc | ttcggggcga | 5940 |
| aaactctcaa | ggatcttacc | gctgttgaga | tccagttcga | tgtaacccac | tcgtgcaccc | 6000 |
| aactgatctt | cagcatcttt | tactttcacc | agcgtttctg | ggtgagcaaa | aacaggaagg | 6060 |
| caaaatgccg | caaaaaaggg | aataagggcg | acacggaaat | gttgaatact | catactcttc | 6120 |
| ctttttcaat | attattgaag | catttatcag | ggttattgtc | tcatgagcgg | atacatattt | 6180 |
| gaatgtattt | agaaaaataa | acaaataggg | gttccgcgca | catttccccg | aaaagtgcca | 6240 |
| cctgacgtc | | | | | | 6249 |

<210> SEQ ID NO 37
<211> LENGTH: 270

```
<212> TYPE: DNA
<213> ORGANISM: Corynebacterium diphtheriae
<220> FEATURE:
<221> NAME/KEY: CDS
<222> LOCATION: (1)..(270)

<400> SEQUENCE: 37 agg gat aaa act aag aca aag ata gag tct ttg aaa gag cat ggc cct      48
Arg Asp Lys Thr Lys Thr Lys Ile Glu Ser Leu Lys Glu His Gly Pro
1               5                   10                  15 atc aaa aat aaa atg agc gaa agt ccc aat aaa aca gta tct gag gaa      96
Ile Lys Asn Lys Met Ser Glu Ser Pro Asn Lys Thr Val Ser Glu Glu
                20                  25                  30 aaa gct aaa caa tac cta gaa gaa ttt cat caa acg gca tta gag cat     144
Lys Ala Lys Gln Tyr Leu Glu Glu Phe His Gln Thr Ala Leu Glu His
            35                  40                  45 cct gaa ttg tca gaa ctt aaa acc gtt act ggg acc aat cct gta ttc     192
Pro Glu Leu Ser Glu Leu Lys Thr Val Thr Gly Thr Asn Pro Val Phe
        50                  55                  60 gct ggg gct aac tat gcg gcg tgg gca gta aac ggt gcg caa gtt atc     240
Ala Gly Ala Asn Tyr Ala Ala Trp Ala Val Asn Gly Ala Gln Val Ile
65                  70                  75                  80 gat agc gaa aca gct gat aat ttg gaa aag                             270
Asp Ser Glu Thr Ala Asp Asn Leu Glu Lys
                85                  90

<210> SEQ ID NO 38
<211> LENGTH: 90
<212> TYPE: PRT
<213> ORGANISM: Corynebacterium diphtheriae

<400> SEQUENCE: 38

Arg Asp Lys Thr Lys Thr Lys Ile Glu Ser Leu Lys Glu His Gly Pro
1               5                   10                  15

Ile Lys Asn Lys Met Ser Glu Ser Pro Asn Lys Thr Val Ser Glu Glu
                20                  25                  30

Lys Ala Lys Gln Tyr Leu Glu Glu Phe His Gln Thr Ala Leu Glu His
            35                  40                  45

Pro Glu Leu Ser Glu Leu Lys Thr Val Thr Gly Thr Asn Pro Val Phe
        50                  55                  60

Ala Gly Ala Asn Tyr Ala Ala Trp Ala Val Asn Gly Ala Gln Val Ile
65                  70                  75                  80

Asp Ser Glu Thr Ala Asp Asn Leu Glu Lys
                85                  90

<210> SEQ ID NO 39
<211> LENGTH: 13
<212> TYPE: PRT
<213> ORGANISM: Corynebacterium diphtheriae

<400> SEQUENCE: 39

Arg Asp Lys Thr Lys Thr Lys Ile Glu Ser Leu Lys Glu
1               5                   10

<210> SEQ ID NO 40
<211> LENGTH: 20
<212> TYPE: PRT
<213> ORGANISM: Corynebacterium diphtheriae

<400> SEQUENCE: 40

Arg Asp Lys Thr Lys Thr Lys Ile Glu Ser Leu Lys Glu His Gly Pro
1               5                   10                  15
```

```
Ile Lys Asn Lys
            20

<210> SEQ ID NO 41
<211> LENGTH: 19
<212> TYPE: PRT
<213> ORGANISM: Corynebacterium diphtheriae

<400> SEQUENCE: 41

Asp Trp Val Ile Arg Asp Lys Thr Lys Thr Lys Ile Glu Ser Leu Lys
1               5                   10                  15

Glu His Gly

<210> SEQ ID NO 42
<211> LENGTH: 4
<212> TYPE: PRT
<213> ORGANISM: Artificial Sequence
<220> FEATURE:
<223> OTHER INFORMATION: synthetic

<400> SEQUENCE: 42

Gly Gly Gly Gly
1

<210> SEQ ID NO 43
<211> LENGTH: 5
<212> TYPE: PRT
<213> ORGANISM: Artificial Sequence
<220> FEATURE:
<223> OTHER INFORMATION: synthetic

<400> SEQUENCE: 43

Gly Gly Gly Gly Gly
1               5

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Gly Gly Lys Gly Gly Gly Gly
1               5

<210> SEQ ID NO 45
<211> LENGTH: 8
<212> TYPE: PRT
<213> ORGANISM: Artificial Sequence
<220> FEATURE:
<223> OTHER INFORMATION: synthetic

<400> SEQUENCE: 45

Gly Gly Gly Asn Gly Ser Gly Gly
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46
```

```
Gly Gly Gly Cys Gly Gly Gly Gly
1               5
```

<210> SEQ ID NO 47
<211> LENGTH: 5
<212> TYPE: PRT
<213> ORGANISM: Artificial Sequence
<220> FEATURE:
<223> OTHER INFORMATION: synthetic

<400> SEQUENCE: 47

```
Gly Pro Asn Gly Gly
1               5
```

VIRAL/BACTERIAL TOXIN POLYPEPTIDES AND METHODS OF USING SAME

STATEMENT AS TO FEDERALLY FUNDED RESEARCH

This invention was made with Government Support under Grant CA60934 from the National Cancer Institute, as well as grants from the National Institute of Allergy and Infectious Disease (Grant Nos. AI021628 and AI057159). The U.S. Government has certain rights in the invention.

CROSS REFERENCE TO RELATED APPLICATIONS

This application is the U.S. National Stage of International Application No. PCT/US2006/033830, filed Aug. 30, 2006, which claims priority to U.S. Ser. No. 11/214,997, filed Aug. 30, 2005, pending, each of which is hereby incorporated by reference.

BACKGROUND OF THE INVENTION

This invention relates to the cytosolic translocation factor complex (CTL) responsible for the translocation of the catalytic domain of diphtheria toxin from the lumen of endosomes to the cytosol.

Diphtheria toxin (DT) (58 kDa) is a typical single chain AB toxin composed of three functional domains: the amino terminal catalytic (C) domain corresponds to fragment A (21 kDa), and the transmembrane (T) and carboxy terminal receptor binding (R) domains comprise fragment B (37 kDa) of the toxin (Choe et al., *Nature* 357: 216-22, 1992). A disulfide bond between Cys 186 and Cys201 subtends a protease sensitive loop and connects fragment A with fragment B. Furin mediated cleavage within this loop and retention of the disulfide bond have been shown to be pre-requisites for intoxication of eukaryotic cells (Tsuneoka et al., *J. Biol. Chem.* 268: 26461-5, 1993; Ariansen et al., *Biochem.* 32:83-90, 1993). Substitution of the native R domain with human interleukin-2 (IL-2) has resulted in the formation of a fusion protein toxin, $DAB_{389}IL-2$, whose cytotoxic action is specifically targeted only to cells expressing the high affinity IL-2 receptors (Bacha et al., *J. Exp. Med.* 167:612-622, 1988; Waters et al., *Eur. J. Immunol.* 20:785-91, 1990; Ratts and vanderSpek, *Diphtheria Toxin: Structure Function and its Clinical Applications. In Chimeric Toxins*, H. Lorberboum-Galski, P. Lazarovici, eds., Taylor and Francis, London, N.Y. p. 14-36, 2002).

The intoxication of eukaryotic cells by diphtheria toxin follows an ordered series of interactions between the toxin and the cell which leads to inhibition of protein synthesis and cell death (Love and Murphy, *Gram-Positive Pathogens*, American Society for Microbiology, Washington, D.C., V. A. Fischetti, J. Rood Ed. pp. 573-582, 2000). Biochemical, genetic and X-ray crystallographic analysis of the toxin has shown the protein to be composed of three distinct domains: an N-terminal catalytic domain (C-domain), a central transmembrane domain (T-domain), and the C-terminal receptor binding domain (R-domain). The intoxication process is initiated by the binding of the toxin to its cell surface receptor, a heparin binding epidermal growth factor-like precursor and CD9. Once bound to its receptor, the toxin is internalized by receptor-mediated endocytosis into an early endosomal compartment (Moya et al., *J. Cell. Biol.,* 101:548, 1985). Upon acidification of the endosomal lumen by vesicular (v)-ATPase, the T-domain undergoes a conformational change and spontaneously inserts into the vesicle membrane forming an 18-22 Å pore or channel (Kagan et al., *Proc. Natl. Acad. Sci., USA,* 78:4950, 1981; Donovan et al., *Proc. Natl. Acad. Sci., USA,* 78:172, 1981). The C-domain, in a fully denatured form, is then specifically thread through this channel and released into the cytosol. Once the C-domain is refolded into an active conformation it catalyzes the $NAD^+$-dependent ADP-ribosylation of elongation factor 2 (EF-2), causing irreversible inhibition of protein synthesis and death of the cell by apoptosis (Pappenheimer, *Annu. Rev. Biochem.,* 46:69, 1977; Kochi and Collier, *Exp. Cell. Res.,* 208:296, 1993).

The requirements for C-domain translocation of diphtheria toxin across endosomal membranes have been partially defined in PCT patent application publication number WO2005014798. In general, non-toxic mutants of diphtheria have fallen into one of two categories: point mutants that no longer catalyze the $NAD^+$-dependent ADP-ribosylation of elongation factor 2 (e.g., CRM197; see Uchida, *J. Biol. Chem.* 248:3838, 1973) and premature chain termination mutants that are no longer capable of binding to the eukaryotic cell surface receptor for the toxin (e.g., CRM45; see Uchida, vide supra). The construction, isolation, and properties of a series of site-directed mutations in transmembrane helix 1 of $DAB_{389}IL-2$ have been previously reported (vanderSpek et al., *Protein Eng.* 7:985, 1994). In this series, the non-toxic $DAB_{389}(L221E)IL-2$ mutant was of particular interest since it was both ADP-ribosyltransferase positive and bound to the targeted high affinity IL-2 receptor with an affinity equal to that of the wild type fusion protein. It was also found that $DAB_{389}IL-2$ binds with greater affinity to its receptor compared to native DT. Therefore, this fusion protein toxin has proven to be an effective probe for studying internalization of the C-domain by target cells (Williams et al., *J. Biol. Chem.* 265:11885-9, 1990).

While much is known about the mechanisms of receptor binding and receptor mediated endocytosis of native DT and the DT-related fusion proteins, less is known about the precise molecular mechanisms of C-domain translocation across the endosomal membrane and its release into the cytosol.

SUMMARY OF THE INVENTION

We hypothesize that there is a common mechanism of catalytic domain entry for bacterial toxins such as, for example, diphtheria, anthrax lethal factor, anthrax lethal edema factor, and the seven serotypes of botulinum toxin, as well as viral transcription factors, such as, for example, HIV-1 reverse transcriptase and Tat, and that that process requires both a cytosolic translocation factor (CTF) complex that includes the COPI coatomer complex, which includes seven coatomer subunits (α, β, β', γ, δ, ε, and ζ), heat shock protein-90 (Hsp90), thioredoxin reductase (TrR-1), and components of the outer surface of endocytic vesicles. Described herein are polypeptides that include a consensus peptide sequence (the entry motif) held in common by these toxins. When administered to an infected cell, these polypeptides can bind to the CTF and inhibit the translocation of DT, or other similar toxins, to the cytosol of the cell, thereby moderating or inhibiting cellular intoxication.

Accordingly, the invention features a polypeptide that includes the sequence of formula I:

$$AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224} \quad (I),$$

where $AA^{215}$ is Thr, Ser, Gly, or Leu; $AA^{216}$ is Glu, Arg, Gln, or Lys; $AA^{217}$ is Lys, Ile, Glu, or Val; $AA^{218}$ is Glu or Asp; $AA^{219}$ is Lys, Glu, His, Leu, Arg, Asn, or Ser; $AA^{220}$ is Phe, Leu, or Ile; $AA^{221}$ is Lys or Arg; $AA^{222}$ is Glu, Asn, Asp, or Lys; $AA^{223}$ is Lys, His, Ser, Ile, or Asn; and $AA^{224}$ is Gly, Leu, Val, Met, or Ile.

In one embodiment, the polypeptide further comprises one or more KXKXX (SEQ ID NO: 5) sequences, where K is Lys and X is any amino acid. In another embodiment, one or more of the KXKXX (SEQ ID NO: 5) sequences are present at the amino terminal or carboxy terminal end of the polypeptide of formula I. In yet another embodiment, the polypeptide of formula I includes one, two, three, or more KXKXX (SEQ ID NO: 5) sequences (e.g., the polypeptide of formula I can include four, five, or six, KXKXX (SEQ ID NO: 5) sequences, or even up to ten KXKXX (SEQ ID NO: 5) sequences). In a preferred embodiment, the polypeptide of formula I includes three KXKXX (SEQ ID NO: 5) sequences.

In another embodiment, the polypeptide has the sequence Thr-Gln-Ile-Glu-Asn-Leu-Lys-Glu-Lys-Gly (SEQ ID NO: 6). In yet another embodiment, the polypeptide has the sequence Thr-Lys-Ile-Glu-Ser-Leu-Lys-Glu-His-Gly (SEQ ID NO: 7). In other embodiments, the polypeptide has the sequence:

```
                                        (SEQ ID NO: 8)
Arg-Asp-Lys-Thr-Lys-Thr-Gln-Ile-Glu-Asn-Leu-Lys-

Glu-Lys-Gly;

(SEQ ID NO: 9)
Arg-Asp-Lys-Thr-Lys-Thr-Lys-Ile-Glu-Ser-Leu-Lys-

Glu-His-Gly;

(SEQ ID NO: 10)
Thr-Gln-Ile-Glu-Asn-Leu-Lys-Glu-Lys-Gly-Pro-Ile-

Lys-Asn-Lys-Met-Ser;

(SEQ ID NO: 11)
Thr-Lys-Ile-Glu-Ser-Leu-Lys-Glu-His-Gly-Pro-Ile-

Lys-Asn-Lys-Met-Ser;

(SEQ ID NO: 12)
Arg-Asp-Lys-Thr-Lys-Thr-Gln-Ile-Glu-Asn-Leu-Lys-

Glu-Lys-Gly-Pro-Ile-Lys-Asn-Lys-Met-Ser;
or
                                        (SEQ ID NO: 13)
Arg-Asp-Lys-Thr-Lys-Thr-Lys-Ile-Glu-Ser-Leu-Lys-

Glu-His-Gly-Pro-Ile-Lys-Asn-Lys-Met-Ser.
```

In yet another embodiment, the polypeptide has the sequence:

```
                                        (SEQ ID NO: 14)
Lys-Thr-Lys-Thr-Lys-Ile-Glu-Ser-Leu-Lys-Glu-His-

Gly-Pro-Ile-Lys-Asn-Lys-Met-Ser-Glu-Ser-Pro-Asn-

Lys-Thr-Val-Ser-Glu-Glu-Lys-Ala-Lys-Gln-Tyr.
```

The invention also features a polypeptide that includes the sequence of formula II:

$$AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224} \quad (II),$$

where $AA^{215}$ is Thr, Ser, Gly, or Leu; $AA^{216}$ is Gln; $AA^{217}$ is Ile, Leu, or Val; $AA^{218}$ is Glu; $AA^{219}$ is Asn; $AA^{220}$ is Leu or Ile; $AA^{221}$ is Lys or Arg; $AA^{222}$ is Glu, Asn, or Asp; $AA^{223}$ is Lys, His, Ser, Ile, or Asn; and $AA^{224}$ is Gly, Leu, Val, Met, or Ile.

In other embodiments, a polypeptide of the invention can be further reacted with a monoclonal antibody, or fragment thereof, to form a covalent bond between the antibody and the polypeptide.

By selectively inhibiting the catalytic domain of toxins or viral factors from translocating across endosomal membranes, a polypeptide of the invention, or derivatives or peptidomimetics thereof, can inhibit mammalian cell death caused by such toxins/factors. Therefore, these polypeptides can be used in the prophylaxis or treatment of diseases caused by toxin-producing bacteria or in the prophylaxis or treatment of adverse events that are caused by the direct exposure of mammals to toxins or toxin derivatives. A polypeptide of the invention can also be used for the prophylaxis or treatment of viral diseases by inhibiting the translocation across endosomal membrane of viral/retroviral transcription factors.

Accordingly, in another aspect, the invention features the use of any of the polypeptides of the invention in the manufacture of a medicament for inhibiting cell death in a mammal, preferably a human. In one embodiment, the polypeptide inhibits the translocation of a viral or bacterial toxin from the lumen of an endosome to the cytosol of a cell. In one example the toxin is an AB toxin, such as, for example, Diphtheria toxin, Botulinum toxin, Anthrax toxin LF, or Anthrax toxin EF. In another embodiment, the polypeptide inhibits the translocation of a viral or retroviral transcription factor, such as, for example, human immunodeficiency virus (HIV-1) reverse transcriptase or Tat.

In another aspect, the invention features a nucleic acid sequence that encodes any of the polypeptide sequences of the invention (for example, those peptides represented by the $AA^{215}$-$AA^{224}$ peptide sequence formula I or II). The polypeptide sequence can be one selected from the group consisting of:

```
                                      (SEQ ID NO: 15)
Thr-Lys-Thr-Gln-Ile-Glu-Gln-Leu-Lys-Glu-Lys-Gly;
                                      (SEQ ID NO: 16)
Arg-Asp-Lys-Thr-Lys-Thr-Gln-Ile-Glu-Gln-Leu-Lys-
Glu-Lys-Gly-Pro-Ile-Lys-Asn-Lys;
                                      (SEQ ID NO: 17)
Asp-Trp-Asp-Val-Ile-Arg-Asp-Lys-Thr-Lys-Thr-Gln-
Ile-Glu-Gln-Leu-Lys-Glu-Lys-Gly;
and
                                      (SEQ ID NO: 18)
Arg-Asp-Lys-Thr-Lys-Thr-Lys-Thr-Gln-Ile-Glu-Gln-
Leu-Lys-Glu-Lys-Gly-Pro-Ile-Lys-Asn-Lys.
```

The peptide sequence can also be Arg-Asp-Lys-Thr-Lys-Thr-Lys-Ile-Glu-Ser-Leu-Lys-Glu-His-Gly-Pro-Ile-Lys-Asn-Lys-Met-Ser (SEQ ID NO: 13).

In another embodiment the nucleic acid is operably linked to an inducible promoter. Examples of inducible promoter systems include those where the expression of the polypeptide sequence can moderated by treating the transfected cell with an agent selected from the group consisting of: doxycycline; retinoic acid; cyclosporin or analogs thereof; FK506; FK520; and rapamycin or analogs thereof.

In another aspect, the invention features a pharmaceutical composition containing a polypeptide of the invention. In one embodiment, the pharmaceutical composition can include agents or compounds that facilitate delivery of the polypeptides to therapeutic targets. Such delivery strategies are described in *Therapeutic Protein and Peptide Formulation* and Delivery (ACS Symposium Series, No 675) (1997), edited by Shahrokh, et al. and in *Formulation and Delivery of Proteins and Peptides* (ACS Symposium Series, No 567) (1994), edited by Cleland and Langer, both of which are hereby incorporated by reference.

In another aspect, the invention features a method of determining whether a compound is capable of inhibiting cell death in a mammal, with the method including the following steps: a) isolating endosomes, desirably early endosomes, comprising a toxin (e.g., a viral or bacterial toxin, preferably an AB toxin, more preferably a Diphtheria toxin, Botulinum toxin, Anthrax toxin LF, or Anthrax toxin EF), from a cell, wherein the endosomes are maintained in a neutral (e.g., about pH 7.0-8.0) or basic pH (e.g., a pH of >7.0, such as 7.5, 8.0, 8.5, or 9.0), b) placing the endosomes in a cytosolic buffer, c) contacting the endosomes with one or more of α-COP, β-COP, β'-COP, γ-COP, δ-COP, ε-COP, ζ-COP, HSP-90, or TrR-1, d) contacting the endosomes with the compound, e) acidifying the endosomes, and f) measuring translocation of the toxin, where a decreased level of translocation relative to that observed in the absence of the compound indicates that the compound inhibits cell death. In a preferred embodiment, the toxin includes a fragment of Diphtheria toxin. In another embodiment, the toxin is a fusion protein-toxin, where the protein includes a binding moiety for a component of the cell membrane of the cell, and the toxin includes a fragment of Diphtheria toxin. In yet another embodiment, the pH of the endosome is maintained at a neutral or basic pH due to the presence of a pH regulator, such as bafilomycin A1. In still another embodiment, the endosome is contacted with a γ-COP subunit. In yet another embodiment, the endosome is contacted with a CTF complex. In still another embodiment, the endosomes are acidified by removing the pH regulator or by adding a mildly acidic solution (e.g., a buffer solution having a pH between about 4.5 and 7.5). An example of an acidic buffer solution includes 10 mM MES, 10 mM Hepes, 120 mM NaCl, 10 mM succinate, and 2 mg/ml glucose, pH 5.0.

In another aspect, the invention features a method of determining whether a compound is capable of promoting cell death in a mammal, with the method including the following steps: a) isolating endosomes, desirably early endosomes, comprising a toxin (e.g., a viral or bacterial toxin, preferably an AB toxin, more preferably a Diphtheria toxin, Botulinum toxin, Anthrax toxin LF, or Anthrax toxin EF), from a cell, wherein the endosomes are maintained in a neutral (e.g., about pH 7.5) or basic pH (e.g., a pH of >7.0, such as 7.5, 8.0, 8.5, or 9.0), b) placing the endosomes in a cytosolic buffer, c) contacting the endosomes with one or more of α-COP, β-COP, β'-COP, γ-COP, δ-COP, ε-COP, ζ-COP, HSP-90, or TrR-1, d) contacting the endosomes with the compound, e) acidifying the endosomes, and f) measuring translocation of the toxin, where an increased level of translocation relative to that observed in the absence of the compound indicates that the compound promotes cell death. In an embodiment, the toxin includes a fragment of Diphtheria toxin. In another embodiment, the toxin is a fusion protein-toxin, where the protein includes a binding moiety for a component of the cell membrane of the cell, and the toxin includes a fragment of Diphtheria toxin. In yet another embodiment, the pH of the endosome is maintained at a neutral or basic pH due to the presence of a pH regulator, such as bafilomycin A1. In still another embodiment, the endosome is contacted with a γ-COP subunit. In yet another embodiment, the endosome is contacted with a CTF complex. In still another embodiment, the endosomes are acidified by removing the pH regulator or by adding a mildly acidic solution (e.g., a buffer solution having a pH between about 4.5 and 7.5). An example of an acidic buffer solution includes 10 mM MES, 10 mM Hepes, 120 mM NaCl, 10 mM succinate, and 2 mg/ml glucose, pH 5.0.

The protein portion of the fusion protein-toxin can be any protein or protein fragment that binds to a component of mammalian cellular membranes and is subsequently internalized. In a desirable embodiment, the protein is IL-2. Other examples include monoclonal antibodies that bind to cellular membrane epitopes. In a most desirable embodiment, the fusion protein-toxin is $DAB_{389}IL-2$ (vanderSpek et al., *J. Biol. Chem.* 269(34):21455-9, 1994). In another embodiment, the cytosolic translocation factor includes γ-COP subunit, Hsp 90, and TrR-1. Assessing translocation can include measuring the ADP-ribosylation of elongation factor-2.

In another aspect, the invention features a composition that contains coatomer, beta subunit (β-COP), or a protein that is substantially identical to β-COP, complexed to a cellular fraction, where the composition is formed by adding β-COP to the cytosol of a mammalian cell, has a molecular weight of between 100 kDa and 250 kDa, and facilitates the translocation of the fusion protein $DAB_{389}IL-2$ from the interior to the exterior of endosomes. In one embodiment, the β-COP that is added is a human recombinant protein. In another embodiment Hsp 90 is also part of the composition. In yet another embodiment, the composition includes TrR-1 and Hsp 90, where both of these components are human recombinant proteins.

In yet another aspect the invention features an interference-nucleotide, such as, for example an iRNA or siRNA, adapted to inhibit or decrease transcription or translation of a factor(s) that is part of the CTF complex (e.g., β-COP, γ-COP, Hsp-90, and TrR-1).

ABBREVIATIONS AND DEFINITIONS

The following abbreviations are used throughout the application: "br" stands for bovine recombinant; when not referring to the amino acid cysteine, "C" stands for catalytic; "CTF" stands for cytosolic translocation factor; "DT" stands for diphtheria toxin; "EF-2" stands for Elongation Factor 2; "ESI" stands for electrospray ionization; "hr" stands for human recombinant; "Hsp" stands for heat shock protein; "MALDI" stands for matrix assisted laser desorption ionization; "MS" stands for mass spectrometry; when not referring to the amino acid threonine, "T" stands for transmembrane; "TrR-1" stands for: thioredoxin reductase; "v" stands for vesicular.

Polypeptides of the present invention include non-naturally occurring (i.e., unnatural) amino acid residues in their D- or L-form such as, for example, homophenylalanine, phenylglycine, cyclohexylglycine, cyclohexylalanine, cyclopentyl alanine, cyclobutylalanine, cyclopropylalanine, cyclohexylglycine, norvaline, norleucine, ornithine, thiazoylalanine (2-, 4- and 5-substituted), pyridylalanine (2-, 3- and 4-isomers), naphthalalanine (1- and 2-isomers) and the like.

By "cytosolic buffer" is meant any buffering system into which endosomes can be placed where they remain intact and viable. In one example, cytosolic buffer includes 3% sucrose in 100 mM HEPES-KOH pH 7.9, 1.4 mM KCl, 30 mM $MgCl_2$, 2 mM EDTA, and 5 mM DTT.

What is meant by "cytosolic translocation factor complex" is a group of component proteins that includes α-COP, β-COP, β'-COP, γ-COP, δ-COP, ε-COP, ζ-COP, Hsp 90 and TrR-1, with the complex also having the ability to facilitate the translocation of the catalytic domain of diphtheria toxin from the interior to the exterior of an endosome.

By a "pharmaceutically acceptable excipient" is meant a carrier that is physiologically acceptable to the treated mammal while retaining the therapeutic properties of the compound with which it is administered. One exemplary pharmaceutically acceptable excipient is physiological saline. Other physiologically acceptable excipients and their formulations are known to one skilled in the art and described, for example, in "Remington: The Science and Practice of Pharmacy" (20th ed., ed. A. R. Gennaro AR., 2000, Lippincott Williams & Wilkins).

By "operably linked" is meant that a nucleic acid molecule and one or more regulatory sequences (e.g., a promoter) are connected in such a way as to permit expression and/or secretion of the product (i.e., a polypeptide) of the nucleic acid molecule when the appropriate molecules (e.g., transcriptional activator proteins) are bound to the regulatory sequences.

By "polypeptide" or "peptide" is meant any chain of natural or unnatural amino acids, regardless of post-translational modification (e.g., glycosylation or phosphorylation), constituting all or part of a naturally-occurring or non-naturally occurring polypeptide or peptide, as is described herein. Naturally occurring amino acids are any one of the following, alanine (A or Ala), cysteine (C or Cys), aspartic acid (D or Asp), glutamic acid (E or Glu), phenylalanine (F or Phe), glycine (G or Gly), histidine (H, or His), isoleucine (I or Ile), lysine (K or Lys), leucine (L or Leu), methionine (M or Met), asparagine (N or Asn), ornithine (O or Orn), proline (P or Pro), hydroxyproline (Hyp), glutamine (Q or Gln), arginine (R or Arg), serine (S or Ser), threonine (T or Thr), valine (V or Val), tryptophan (W or Trp), or tyrosine (Y or Tyr).

By "substantially identical" is meant a protein, polypeptide, or nucleic acid exhibiting at least 75%, but preferably 85%, more preferably 90%, most preferably 95%, or even 99% identity to a reference amino acid or nucleic acid sequence (e.g., any one of the proteins, polypeptides, or nucleic acids described herein). For polypeptides, the length of comparison sequences will generally be at least 10 amino acids, and preferably at least 20 amino acids. For nucleic acids, the length of comparison sequences will generally be at least 30 nucleotides, preferably at least 60 nucleotides, and more preferably at least 120 nucleotides.

BRIEF DESCRIPTION OF THE DRAWINGS

FIG. 1A shows autoradiographs of the in vitro translocation of the C-domain from either $DAB_{389}$IL-2 or $DAB_{389}$(L221E)IL-2 (the non-toxic, translocation deficient mutant) from the lumen of early endosomes to the external milieu, assayed as previously described by Ratts et al. (*J. Cell Biol.* 160:1139, 2003). In this assay, the early endosomal compartment of Hut102/6TG cells was pre-loaded with fusion protein toxin in the presence of Bafilomycin A1. Following cell lysis and partial purification of early endosomes by sucrose density gradient centrifugation, the specific translocation of the C-domain to the external milieu was determined after the addition of both ATP (A) and either crude cytosol (C) or partially purified cytosolic translocation factor (ppCTF) complex to the reaction mixture. ADP-ribosyltransferase activity associated with the pellet (P) and supernatant fluid fractions were monitored by autoradiography following incorporation of [$^{32}$P]-ADP-ribose into elongation factor 2.

FIG. 1B is a graph showing the sensitivity of Hut102/6TG and Hut102/6TG-T1 cells to $DAB_{389}$IL-2 by dose response analysis. The early endosomal compartment in Hut102/6TG cells was pre-loaded with either Oregon Green (OG) 514 conjugated to 70 kD dextran in the absence or presence of either $DAB_{389}$IL-2 or $DAB_{389}$(L221E)IL-2 in the presence of Bafilomycin A1. Following cell lysis and partial purification of the early endosome fraction by sucrose density gradient centrifugation, endosomes pre-loaded with OG514 dextran conjugate alone were resuspended in translocation buffer in the absence (▲) or presence (○) of 2 mM ATP. Endosomes that were pre-loaded with either OG514 conjugate and $DAB_{389}$IL-2 (■) or OG514 conjugate and $DAB_{389}$(L221E) IL-2 (◇) were resuspended in translocation buffer in the presence of 2 mM ATP. Partially purified early endosomes that were not pre-loaded with OG514-dextran are indicated by the symbol (●). Fluorescence Emission was measured at an excitation wavelength of 511 nm and an emission wavelength of 530 nm. Values were compared to 1 ng/ml OG 514 conjugate standards at pH 7.5 and 4.5.

FIG. 2 is a graph showing the dose response of Hut102/6TG (●), Hut102/6TG-T1 (■), and Hut102/6TG-T1/pRR-XT1 (▲) cells to the fusion protein toxin $DAB_{389}$IL-2. Individual cell lines were seeded at $5\times10^4$ cells per well in 96 well plates and incubated in the absence of presence of varying concentrations of $DAB_{389}$IL-2 for 18 hrs at 37° C. in 5% $CO_2$. Cells were then washed and resuspended in minimal (leucine depleted) medium containing [$^{14}$C]-leucine and pulse labeled for 2 hrs at 37° C. in 5% $CO_2$. Cells were then lysed with 0.4M KOH, incubated for 10 min, and total protein was precipitated by the addition of 10% trichloroacetic acid (TCA). Protein precipitates were collected on glass fiber filters (Whatman GF/A) using a PhD cell harvester and radioactivity was measured according to standard methods. Cells incubated in medium alone served as controls. The results from three separate experiments in which each fusion protein toxin concentration was assayed in quadruplicate are presented. Results are presented as percent control level of [$^{14}$C]-leucine incorporation.

FIG. 3A is an autoradiograph showing the interaction of β-COP with DT140-271 in GST-pull down experiments. GST or the fusion protein GST-DT140-271 was expressed in recombinant *E. coli* and purified by affinity chromatography on glutathione-Sepharose columns. Purified recombinant protein was then applied to GST-beads. Cellular extracts from Hut102/6TG cells were passed over the columns and eluted by the addition of reduced glutathione. Fractions were analyzed by SDS-polyacrylamide gel electrophoresis and immunoblot using anti-β-COP antibodies. (B)

FIG. 3B is a electrophoresis gel showing the interaction of β-COP with GST-DT140-271 in pull down experiments using cellular extracts from Hut102/6TG cells in the absence and presence of increasing concentrations of the synthetic "translocation motif" peptide T1 (SEQ ID NO: 2). The concentration of T1 peptide added to the pull down reaction mix is shown in parentheses.

FIG. 4 is a schematic showing the pTRACER-CMV2 expression vector and the oligonucleotide primers used in PCR amplification of amino acids 210-229 from $DAB_{389}$IL-2.

DETAILED DESCRIPTION

In the present invention, the in vitro C-domain translocation assay described by Ratts et al. (*J. Cell Biol.* 160:1139, 2003) was used to further characterize the interaction between $DAB_{389}$(L221E)IL-2 and Hut102/6TG cells. In these experiments, early endosomes in Hut102/6TG cells were separately pre-loaded with either $DAB_{389}$IL-2 or $DAB_{389}$(L221E)IL-2 in the presence of Bafilomycin A1.

Cells were lysed and early endosomes were partially purified by sucrose density centrifugation. Upon removal of Bafilomycin A1 and the addition of both ATP and partially purified CTF complex, translocation and release of the C-domain from the endosomal lumen to the external milieu was measured by determining the ADP-ribosyltransferase activity in both the pellet and supernatant fluid fractions following ultracentrifugation. Since translocation and refolding of the C-domain into a biologically active conformation have been shown previously to be mutually exclusive events (Ratts et al., vide supra), crude cytosolic extracts were added prior to the ADP-ribosylation assay. As shown in FIG. 1A, approximately 60% of the ADP-ribosyltransferase activity from $DAB_{389}$IL-2 was translocated from the endosomal lumen to the external medium in the 30 min incubation period. In marked contrast, essentially all of the ADP-ribosyltransferase activity from $DAB_{389}$(L221E)IL-2 remained in the pellet fraction, demonstrating that the non-toxic phenotype of this mutant results from a defect in C-domain translocation across the endosomal vesicle membrane and release into the surrounding medium.

In order to further examine whether or not the T-domain of $DAB_{389}$(L221E)IL-2 is capable of inserting into the vesicle membrane and forming ion conductive channels, this peptide was co-internalized with the pH sensitive dye Oregon Green 514 (OG 514) conjugated to high molecular weight dextran (70 kDa) into early endosomes, which were then monitored for acidic pH quenching of the fluorescent signal upon addition of ATP to the reaction mixture. For early endosomes that were pre-loaded with OG515-dextran alone, the fluorescent signal remained constant in the absence of added ATP. For endosomes to which ATP was added, a progressive quenching of the fluorescent signal was observed over time (see FIG. 1B). Co-internalization of OG514-dextran with either $DAB_{389}$IL-2 or $DAB_{389}$(L221E)IL-2 into early endosomes, followed by the addition of ATP to the reaction mixture, resulted in the virtual identical quenching of the fluorescent signal. In both instances, quenching of the fluorescent signal was seen for the first 5 minutes after which the signal remained relatively constant, presumably due to an equilibration of the luminal pH caused by an influx of protons into the endosomal lumen through the continuous action of the v-ATPase proton pump and the efflux of protons to the external milieu through the nascent channel formed by the membrane insertion of the diphtheria toxin T-domain. Taken together, these results suggest that both the wild type and mutant fusion protein toxins are capable of forming ion conductive channels in the endosomal vesicle membrane. These results also suggest that the non-cytotoxic phenotype of $DAB_{389}$(L221E) IL-2 is due to a specific defect in C-domain translocation and release into the cytosol of target cells.

Some AB toxins are known to employ a common route of entry into the cell requiring passage through an acidified early endosomal compartment, (Pappenheimer, Annu. Rev. Biochem. 46:69, 1977; Wesche et al., Biochemistry 37:15737, 1998; Bade et al., Naunyn. Schmiedebergs Arch. Pharmacol. 365:R13, 2002). Further, in all instances where this is so, the putative "translocation motif" is positioned in a region of these protein toxins consistent with their emergence on the cytosolic side of the endosomal membrane early in the delivery process. It is of particular interest to note that the L221E mutation in $DAB_{389}$IL-2, which gives rise to a translocation deficient phenotype as described above, is contained within the most highly conserved region in the motif. In anthrax lethal factor the putative "translocation motif" is positioned between residues 28-39 in the mature protein, a region that is structurally distinct from the protective antigen binding domain (Lacey et al., J. Biol. Chem. 277:3006, 2002). In addition, N-terminal deletion analysis of anthrax lethal factor has shown previously that this region is required for toxicity (Arora and Leppla, Infect. Immun. 62:4955, 1994). In contrast, this translocation motif was not detected in those protein toxins known to undergo retrograde transport and whose catalytic domains enter the cytosol from the endoplasmic reticulum (e.g., cholera toxin, Shiga toxin, ricin toxin, Pseudomonas exotoxin A).

The potential role for the "translocation motif" in mediating delivery of the diphtheria toxin C-domain across early endosomal membrane was further explored by constructing a gene encoding a peptide encompassing amino acids 210-229 of diphtheria toxin. The PCR primer used for the 5'-end of this construct introduced a Kozak sequence and translation initiation signal to ensure expression of the peptide as well as an EcoRI restriction endonuclease site (Kozak, J. Biol. Chem. 266:19867, 1991). The PCR primer for the 3' end of the mini-gene included a transcription termination signal and an XbaI restriction endonuclease site. Following PCR amplification and hybridization, double stranded oligonucleotides were digested with EcoRI and XbaI, and ligated into the corresponding restriction sites in the pTRACER CMV2 vector. The TOP10 strain of E. coli was then transformed and single colonies were selected on LB agar medium supplemented with 100 μg/mL ampicillin. Individual clones were isolated and plasmid DNA was prepared and sequenced to insure that a single copy of the mini-gene encoding the putative "translocation motif" was inserted in the proper orientation and retained the correct reading frame. A single plasmid preparation was then selected, designated pTRACER-T1, and used to transfect Hut102/6TG cells (see Methods section).

Stable transfectants were selected in the presence of Zeocin, and insertion of pTRACER-T1 DNA into the genome was phenotypically confirmed by both the constitutive expression of green fluorescent protein (GFP) and resistance to Zeocin. Individual transfectant cell lines were then isolated by limit dilution. To demonstrate the presence of mRNA specific for T1 mini-gene expression, total mRNA was partially purified from Hut102/6TG and Hut102/6TG-T1 cells and oligonucleotide primers specific for the 5'-end of the T1 mini-gene and 3'-end vector sequences were used for PCR amplification. mRNA encoding the T1 mini-gene was detected in extracts of Hut102/6TG-T1 cells, but not in extracts of the parental Hut102/6TG cell line.

Figure 2:
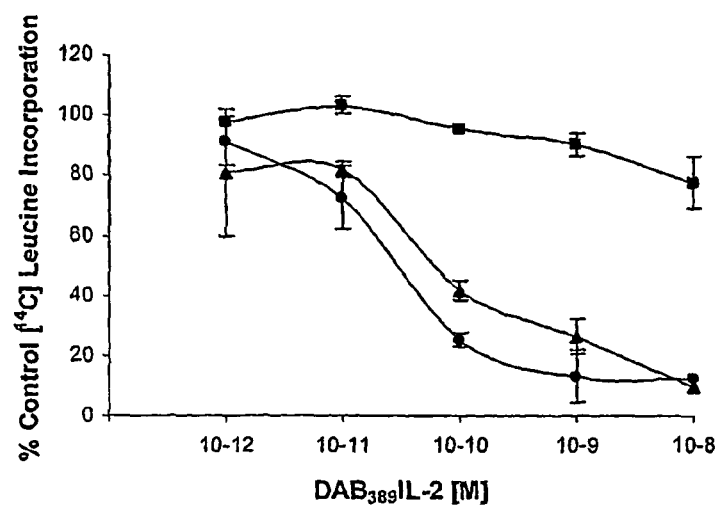

Hut102/6TG and Hut102/6TG-T1 cells were then examined for their sensitivity to $DAB_{389}$IL-2 by dose response analysis (see Example 3). As shown in FIG. 2, the $IC_{50}$ for $DAB_{389}$IL-2 in Hut102/6TG cells was found to be $5 \times 10^{-11}$ M. In marked contrast, the $IC_{50}$ for $DAB_{389}$IL-2 in Hut102/6TG-T1 cells was greater than $10^{-8}$M. Analogous results were obtained when the parental and transfectant cell lines were challenged with native diphtheria toxin.

To further demonstrate that expression of the "translocation motif" mini-gene was directly associated with the toxin resistant phenotype, Hut102/6TG-T1 cells were transfected with plasmid pRR-XT1, which produces siRNA specific for knock down of the "translocation motif" transcripts (see Methods section). Co-expression of siRNA specific for T1 mini-gene expression in Hut102/6TG-T1 cells results in the restoration of full sensitivity to $DAB_{389}$IL-2 ($IC_{50} \sim 7 \times 10^{-11}$M). These results demonstrate that the toxin resistant phenotype in Hut102/6TG-T1 cells is directly related to the expression of the "translocation motif" in target cells. Taken together the above observations support the hypothesis that the putative "translocation motif" within transmembrane helix 1 of the diphtheria toxin T-domain plays an essential role in the delivery of the C-domain from the lumen of acidified early endosomes to the cytosol in vivo.

In order to isolate other potential cytosolic T1 binding proteins, a fusion protein between glutathione S-transferase (GST) and diphtheria toxin sequences 140 to 271 was constructed. Following expression and purification of the GST-DT140-271 fusion protein from extracts of recombinant *E. coli*, a series of pull down experiments in post-nuclear supernatant extracts of Hut102/6TG cells were conducted. Following SDS-polyacrylamide gel electrophoresis, immunoblot analysis using an anti-β-COP antibody (obtained from Abcom, Cambridge, UK), revealed individual β-COP-containing proteins that were specifically bound to the DT140-271 portion of the fusion protein (see FIG. 3A). These proteins were further identified by mass spectrometry sequence analysis. The identification of β-COP in pull down mixtures was of particular interest since Lemichez et al., *Mol. Microbiol.* 23:445, 1997 demonstrated that C-domain translocation was inhibited by the addition of anti-β-COP to the in vitro translocation reaction mixture.

Figure 3:
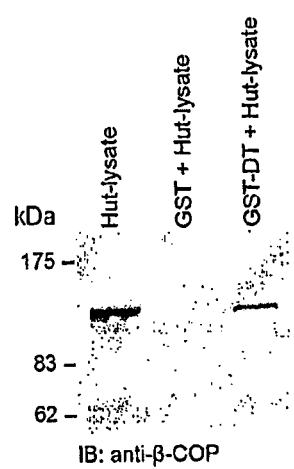
Figure 3:
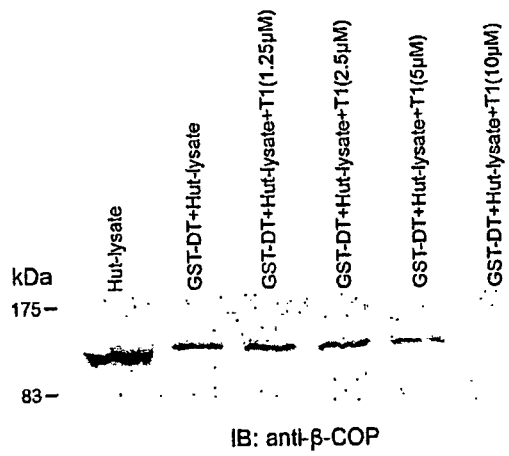

In order to further explore the interaction between β-COP and DT140-271 sequences, the inhibition of this interaction by the addition of the synthetic T1 peptide to the pull down mixture was investigated. In these experiments the T1 peptide was added to post-nuclear supernatant extracts of Hut102/6TG cells and incubated for 1 hr at 4° C., GST-DT140-271 was added and following a 1 hour incubation at 4° C., proteins that were pulled down were separated by electrophoresis on SDS-polyacrylamide gels and analyzed by immunoblot using anti-β-COP. As shown in FIG. 3B, in the absence of the T1 peptide, GST-DT140-271 specifically interacts with and pulls down β-COP from Hut102/6TG extracts. In marked contrast, addition of increasing concentrations of T1 peptide (1.25 μM-10 μM) to the pull down reaction mixture inhibits this interaction in a dose dependent manner. In control experiments a peptide of similar molecular weight and pI as T1, failed to block the pull down of β-COP by GST-DT140-271. Taken together these results strongly suggest that the interaction between β-COP and DT140-271 at least overlaps with the "translocation motif" sequence. In addition, these results also demonstrate that, like Hsp 90 and thioredoxin reductase, β-COP plays a direct role in C-domain translocation from the lumen of early endosomes and serves as an essential component of the cytosolic translocation factor (CTF) complex.

Since the results presented above support the hypothesis that C-domain translocation and release into the cytosol requires assistance of a CTF complex of proteins, it was reasoned that the toxin might carry a specific motif that interacts with one or more of the components of this complex. In an attempt to identify a putative "translocation motif" we compared by BLAST [Basic Local Alignment Search Tool (Altschul et al., *J. Mol. Biol.* 215:403, 1990)] analysis a family of overlapping 12 amino acid sequences, each of which separated by 3 amino acids, of diphtheria toxin against the sequence of other bacterial protein toxins. A consensus sequence for the motif (SEQ ID NO: 1) was identified using the Multiple Expectation maximization for Motif Elucidation (MEME) tool (Bailey and Elkan, *Proceedings of the Second International Conference on Intelligent Systems for Molecular Biology*, AAAI Press, Menlo Park, Calif., pp. 28-36, 1994). As shown in Table 1, position-specific-iterated (PSI)-BLAST (Karlin and Altschul, *Proc. Natl. Acad. Sci, USA* 87:2264, 1990) and AlignX (Vector NTI, version 6) computational analysis indicated a statistically significant conserved 10 amino acid peptide motif present in transmembrane helix T1 (TH1) of diphtheria toxin with dodecamer sequences in anthrax lethal and edema factors, as well as the botulinum neurotoxin serotypes A, C, and D.

TABLE 1

Results of position-specific-iterated (PSI)-BLAST and AlignX computational analysis of native diphtheria toxin

| Toxin[1] | Residue numbers | Sequence |
|---|---|---|
| Anthrax Edema Factor (P40136) | 50-65 | EKNKTEKEKFKDSINN (SEQ ID NO: 19) |
| Anthrax Edema Factor (P40136) | 404-420 | KLDHLRIEELKENGII (SEQ ID NO: 20) |
| Anthrax Lethal Factor (YP_016503) | 60-75 | ERNKTQEEHLKEIMKH (SEQ ID NO: 21) |
| Botulinum neurotoxin Serotype A (P10845) | 719-734 | AKVNTQIDLIRKKMKE (SEQ ID NO: 22) |
| Botulinum neurotoxin Serotype A (P10845) | 828-843 | GTLIGQVDRLKDKVNN (SEQ ID NO: 23) |
| Botulinum neurotoxin Serotype C1 (P18640) | 755-770 | ENIKSQVENLKNSLDV (SEQ ID NO: 24) |
| Botulinum neurotoxin Serotype D (P19321) | 751-766 | ENIKSQVENLKNSLDV (SEQ ID NO: 25) |
| Diphtheria toxin (AAV70486) | 211-226 | DKTKTKIESLKEHGPI (SEQ ID NO: 26) |
| Consensus | | ----TQIENLKEKG-- (SEQ ID NO: 2) |

[1]Database ascension numbers are given in parentheses

Polypeptides of Formula I and II

The importance of the binding of a conserved peptide sequence found in diphtheria toxin, as well as other toxins, to a cytosolic translocation factor for cellular intoxication has been demonstrated herein. In addition, a consensus sequence for this conserved region has been identified. Accordingly, in a first aspect, the invention features polypeptides of formula I:

$$AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224} \quad \text{(I)},$$

where $AA^{215}$ is Thr, Ser, Gly, or Leu; $AA^{216}$ is Glu, Arg, Gln, or Lys; $AA^{217}$ is Lys, Ile, Glu, or Val; $AA^{218}$ is Glu or Asp; $AA^{219}$ is Lys, Glu, His, Leu, Arg, Asn, or Ser; $AA^{220}$ is Phe, Leu, or Ile; $AA^{221}$ is Lys or Arg; $AA^{222}$ is Glu, Asn, Asp, or Lys; $AA^{223}$ is Lys, His, Ser, Ile, or Asn; and $AA^{224}$ is Gly, Leu, Val, Met, or Ile.

The invention also features a polypeptide that includes the sequence of formula II:

$$AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224} \quad \text{(II)},$$

where $AA^{215}$ is Thr, Ser, Gly, or Leu; $AA^{216}$ is Gln; $AA^{217}$ is Ile, Leu, or Val; $AA^{218}$ is Glu; $AA^{219}$ is Asn; $AA^{220}$ is Leu or Ile; $AA^{221}$ is Lys or Arg; $AA^{222}$ is Glu, Asn, or Asp; $AA^{223}$ is Lys, His, Ser, Ile, or Asn; and $AA^{224}$ is Gly, Leu, Val, Met, or Ile.

Methods of Inhibiting Cell Death by Administration of Polypeptides of the Invention The present invention also provides methods of inhibiting cell death in a mammal, preferably a human, by administering to the cell a polypeptide of the invention, or analog thereof, which inhibits the translocation of the catalytic domain of a toxin from the lumen of endosomes to the cytosol of the cell. In one example, the toxin is an AB toxin, such as, for example Diphtheria toxin, one of the seven serotypes of Botulinum toxin, Anthrax toxin LF, or Anthrax toxin EF. In another embodiment, the polypeptide inhibits the translocation of a viral or retroviral transcription factor, such as, for example, human immunodeficiency virus (HIV-1) reverse transcriptase or Tat. Polypeptides of the invention include peptide sequences that contain the entry motif consensus sequence (e.g., TQIENLKENG; (SEQ ID NO: 27)) or the entry motif consensus sequence with one or more KXKXX (SEQ ID NO: 5) motifs (e.g., 1, 2, 3, 4, 5, 6, or more). Polypeptides of the invention also include peptidyl compounds that are further modified to improve their pharmacological properties, as described in detail herein. The invention also features nucleic acid sequences that encode the polypeptides having the entry motif consensus sequence, as well as, nucleic acid sequences that interfere with the translation of translocation factors, such as, for example, β-COP, γ-COP, Hsp 90, and TrR-1.

Modifications of Polypeptides of Formula I and II

It is possible to modify the structure of a polypeptide of the invention for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of CTF. Such modified peptides can be produced, for instance, by amino acid substitution, deletion, or addition.

For example, in a polypeptide of the invention that inhibits translocation from the endosome to the cytosol of a cell (e.g., a polypeptide of formula I or II), it is reasonable to expect that an isolated replacement of a leucine with an isoleucine or valine, an aspartate with a glutamate, a threonine with a serine, or a similar replacement of an amino acid with a structurally related amino acid will not have a major effect on the ability of the peptide to serve as an inhibitor. Conservative replacements or substitutions are those that take place within a family of amino acids that are related in their side chains, and apply to those that result from genetically encoding or those that are synthetically produced. Amino acids can be divided into four families: (1) acidic residues, such as aspartatic acid or glutamic acid; (2) basic residues, such as lysine, arginine, or histidine; (3) nonpolar residues, such as alanine, valine, leucine, isoleucine, proline, phenylalanine, methionine, or tryptophan; and (4) uncharged polar residues, such as glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic residues, such as aspartate, glutamate; (2) basic residues, such as lysine, arginine histidine, (3) aliphatic residues, such as glycine, alanine, valine, leucine, isoleucine, serine, threonine, with serine and threonine optionally be grouped separately as aliphatic-hydroxyl; (4) aromatic residues, such as phenylalanine, tyrosine, tryptophan; (5) amide residues, such as asparagine, glutamine; and (6) sulfur-containing residues, such as cysteine and methionine (see, for example, Biochemistry, 2nd ed., Ed. by L. Stryer, W H Freeman and Co.: 1981). Alternatively, amino acid replacement can be based on steric criteria, e.g. isosteric replacements, without regard for polarity or charge of amino acid sidechains.

Thus, one or more amino acid residues in a polypeptide of the invention can be replaced with another amino acid residue from the same family. Alternatively, in another embodiment, mutations can be introduced randomly along all or part of a nucleic acid encoding a polypeptide of the invention, such as by saturation mutagenesis, and the resultant mutants can be screened for their ability to inhibit translocation, by methods described herein. Following mutagenesis of the nucleic acid encoding the CTF peptide, the peptide can be expressed by any recombinant technology known in the art, and the activity of the peptide can be determined.

The polypeptides of the present invention include analogs that contain moieties that improve pharmacodynamic properties, such as, for example, those that increase in vivo half-life; or that improve physical properties, such as, for example, increased resistance to in vivo degradation or increased cell-membrane permeability.

In one example, polymer vehicles may be used to modify the polypeptides of the present invention. Various means for attaching chemical moieties useful as vehicles are currently available, see e.g., Patent Cooperation Treaty ("PCT") International Publication No. WO 96/11953, entitled "N-Terminally Chemically Modified Protein Compositions and Methods." This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa. The PEG groups will generally be attached to the compounds of the invention via acylation or reductive alkylation through a reactive group on the PEG moiety (e.g., an aldehyde, amino, isothiocyanate, or an activated carboxylic acid) to a reactive group on the inventive compound (e.g., an amino, or activated carboxyl group).

A useful strategy for the PEGylation of synthetic peptides consists of combining, through forming a conjugate linkage in solution, a peptide and a PEG moiety, each bearing a special functionality that is mutually reactive toward the other. The peptides can be prepared by solid phase synthesis, as described herein. Through selective deprotection strategies, the peptides are "preactivated" with an appropriate functional group at a specific site. The precursors can be purified and fully characterized prior to reacting with the PEG moiety. Ligation of the peptide with PEG usually takes place in aqueous phase and can be easily monitored by reverse phase analytical HPLC. In a desirable embodiment, the PEG moiety contains functionality reactive towards functional groups contained on biomolecules (e.g. proteins, aminoglycosylglycans), making this moiety a heterobifunctional crosslinker. Preferably, the reactive functionality on the PEG moiety is a maleimide, vinyl carbonyl, vinyl sulfonyl group, or alpha-halocarbonyl, and is reacted with a biomolecule containing a free thiol. Such reactions are extremely facile and can be performed at low reactant concentrations, such as are found in in vitro experiments or in vivo.

Other bifunctional agents are known to be useful for cross-linking the peptides or their functional derivatives to a water-insoluble support matrix or to other macromolecular vehicles. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Also included are alkyl linkers such as —NH—$(CH_2)_5$C(O)—. These alkyl linkers may further be substituted by any non-sterically hindering group such as $C_{1-6}$ alkyl, $C_{2-7}$ acyl, halogen (e.g., Cl, Br), CN, $NH_2$, aryl, heterocyclyl, etc.

Other linkers include those made up of amino acids linked together by amide bonds. In one example, the linker is made up of from 1 to 20 amino acids linked by amide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly_4)$ (SEQ ID NO: 42), $(Gly)_5$ (SEQ ID NO: 43)), poly(Gly-Ala), and polyalanines. Other specific examples of linkers are: $(Gly)_3Lys(Gly)_4$ (SEQ ID NO: 44); $(Gly)_3AsnGlySer(Gly)_2$ (SEQ ID NO: 45); $(Gly)_3Cys(Gly)_4$ (SEQ ID NO: 46); and GlyProAsnGlyGly (SEQ ID NO: 47). In some examples, the peptide linker is designed to be cleaved in vivo at a specific dipeptide amide bond by proteolytic enzymes.

Polysaccharide polymers are another type of water soluble polymer which may be used for modification of the polypeptides of the invention. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (see, for example, WO 96/11953 and WO 96/05309). The use of dextran conjugated to therapeutic or diagnostic immunoglobulins has been reported; see, for example, European Patent Publication No. 0 315 456. Dextran of about 1 kD to about 20 kD is preferred when dextran is used as a vehicle in accordance with the present invention.

Other carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the polypeptide of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

In other examples, a polypeptide of the invention can be modified by the replacement of one or more peptidyl (—C(O)NR—) linkages (bonds) by a non-peptidyl linkage. Exemplary non-peptidyl linkages are —$CH_2$-carbamate (—$CH_2$—OC(O)NR—), phosphonate, —$CH_2$-sulfonamide (—$CH_2$—S(O)$_2$NR—), urea (—NHC(O)NH—), —$CH_2$-secondary amine, and alkylated amide [—C(O)NR$^A$— wherein R$^A$ is alkyl).

In other examples, one or more individual amino acid residues can be modified. Various derivatizing agents are known to react specifically with selected sidechains or terminal residues. For example, lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been performed, with examples including introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide, followed by reaction with an amine to form an amide.

Nucleic Acids Encoding PolyPeptide Sequences of the Invention

Cell death in a mammal can be inhibited by administering to the cell a nucleic acid sequence that encodes a polypeptide that inhibits the translocation of the catalytic domain of a toxin or a transcription factor from the lumen of endosomes to the cytosol of a mammalian cell. Examples are polypeptides that include the amino acid sequences of Formula I or II.

The nucleic acid sequences of the present invention or portions thereof can be inserted into a vector used to propagate the sequences in a cell. Such vectors are introduced into cells (e.g., prokaryotic or eukaryotic), and the cells are propagated to produce multiple copies of the vector. A useful type of vector is an expression vector. Coding regions of the nucleic acid sequences of the present invention or fragments thereof can be inserted into an expression vector under conditions appropriate for expression of the sequences. Such vectors, are introduced into cells (e.g., prokaryotic or eukaryotic cells) under conditions appropriate for expression. In one embodiment, the cell is eukaryotic (e.g., mammalian, avian, insect, or yeast). In a preferred embodiment, the cell is a human cell.

The invention thus provides nucleic acid constructs which encode the various polypeptides, or fragments thereof, of the invention, various DNA vectors containing those constructs for use in transducing prokaryotic and eukaryotic cells, cells transduced with the nucleic acids, fusion proteins encoded by the above nucleic acids, and target gene constructs.

Each of the nucleic acids of this invention may further contain an expression control sequence operably linked to the coding sequence and may be provided within a DNA vector, e.g., for use in transducing prokaryotic or eukaryotic cells. Some or all of the nucleic acids of a given composition, including any optional nucleic acids, may be present within a single vector or may be apportioned between two or more vectors. In certain embodiments, the vector or vectors are viral vectors useful for producing recombinant viruses containing one or more of the nucleic acids. The recombinant nucleic acids may be provided as inserts within one or more recombinant viruses which may be used, for example, to transduce cells in vitro or cells present within an organism, including a human or non-human mammalian subject. For example, nucleic acids encoding peptides or peptidyl fragments of the present invention may be present within a single recombinant virus or within a set of recombinant viruses, each of which containing one or more of the set of recombinant nucleic acids. Viruses useful for such embodiments include any virus useful for gene transfer, including adenoviruses, adeno-associated viruses (AAV), retroviruses, hybrid adenovirus-AAV, herpes viruses, lenti viruses, etc. In specific embodiments, the recombinant nucleic acid containing the target gene is present in a first virus and one or more or the recombinant nucleic acids encoding the transcription regulatory protein(s) are present in one or more additional viruses. In such multiviral embodiments, a recombinant nucleic add encoding a fusion protein containing a bundling domain and a transcription activation domain, and optionally, a ligand binding domain, may be provided in the same recombinant virus as the target gene construct, or alternatively, on a third virus. It should be appreciated that non-viral approaches (naked DNA, liposomes or other lipid compositions, etc.) may be used to deliver nucleic acids of this invention to cells in a recipient organism.

The invention also provides methods for rendering a cell capable of regulating expression of a target gene which involves introducing into the cell one or more of the nucleic acids of this invention to yield engineered cells which can express the appropriate fusion protein(s) of this invention to regulate transcription of a target gene. The recombinant nucleic acid(s) may be introduced in viral or other form into cells maintained in vitro or into cells present within an organism. The resultant engineered cells and their progeny containing one or more of these recombinant nucleic acids or nucleic acid compositions of this invention may be used in a variety of important applications, including human gene therapy, analogous veterinary applications, the creation of cellular or animal models (including transgenic applications) and assay applications. Such cells are useful, for example, in methods involving the addition of a ligand, preferably a cell permeant ligand, to the cells (or administration of the ligand to an organism containing the cells) to regulate expression of a target gene. Particularly important animal models include rodent (especially mouse and rat) and non-human primate models.

The coding sequence of the polypeptides of the invention can be placed under the control of a strong constitutive or inducible promoter or promoter/enhancer to achieve expression, and preferably secretion, of the polypeptides of the invention. In certain gene therapy applications, the cells are human and a nucleic acid of the present invention is operably linked to an inducible promoter. Such inducible promoters are known to those skilled in the art. For example, the tetracycline-inducible system of Gossen and Bujard (*Proc. Natl. Acad. Sci. USA* 89:5547-5551, 1992; U.S. Pat. No. 5,464, 758), has been used to regulate inducible expression of several genes (Furth et al., *Proc. Natl. Acad. Sci. USA* 91:9302-9306, 1994; Howe et al., *J. Biol. Chem.* 270:14168-14174, 1995; Resnitzky et al., *Mol. Cell. Biol.* 14:1669-1679, 1994; Shockett et al., *Proc. Natl. Acad. Sci. USA* 92:6522-6526, 1995). This system uses a chimeric transcription factor, termed tTA, which is composed of the repressor of *Escherichia coli* (*E. coli*) tetracycline-resistance operon (tetR) and the activation domain (carboxyl terminal domain) of virion protein 16 (VP16) of herpes simplex virus (HSV) (Triezebberg et al., *Genes Dev.* 2:718-729, 1988). The gene of interest is placed downstream of a minimal cytomegalovirus (CMV) 1A promoter, derived from the immediate early CMV genes, which is linked to multiple copies of tetO, the binding site for the tetracycline repressor tetR. In the absence of tetracycline, the tetR portion of the transactivator binds the tetO sequences of the promoter and the VP16 portion facilitates transcription. When tetracycline is present, tetracycline binds the tetR portion of tTA, which in turn prevents binding of the tetR portion to the tetO sequence(s) of the promoter, thus inhibiting transcription. Since even low concentrations of tetracycline are sufficient to block tTA function and since most mammalian cells can tolerate tetracycline, this system provides a tightly regulated on/off switch for gene expression that can be controlled by varying the tetracycline concentration to which the cells are exposed. This work has been extended by Yee et al, U.S. Pat. No. 6,432,705, who describe an inducible promoter activated by a multi-chimeric transactivator that is particularly in the expression of retroviral vectors.

A variety of other regulatable expression systems have been described involving allostery-based switches triggered by tetracycline, RU486 or ecdysone, as well as dimerization-based switches triggered by dimerizing agents such as rapamycin, coumermycin, dimers of FK506, synthetic FKBP-binders and/or CsA, or analogs thereof (see, for example, Clackson, *Current Opinion in Chemical Biology* 1:210-218, 1997) U.S. Pat. No. 6,566,073 describes methods for producing target proteins in vivo using fusion proteins containing conditional retention domains. Illustrative examples of ligand binding domain/ligand pairs include retinol binding protein or variants thereof and retinol or derivatives thereof, cyclophilin or variants thereof and cyclosporin or analogs thereof; FKBP or variants thereof and FK506, FK520, rapamycin, analogs thereof or synthetic FKBP ligands.

Polypeptides of the Invention that are Interference-Nucleotides

In another aspect the invention features interference-nucleotides, such as, for example iRNA or siRNA adapted to inhibit or decrease the transcription of factors that are part of the CTF complex (e.g., β-COP, Hsp-90, and TrR-1). These vectors may be produced via standard recombinant techniques, taking into account the published nucleic acid sequence data for such genes (for β-COP see Duden et al., *Cell* 64(3):649-65, 1991; for Hsp 90 see Rebbe et al., *J. Biol. Chem.* 264(25):15006-11, 1989; for thioredoxin reductase see Gadaska et al., FEBS Lett. 303:5-9, 1995), standard cloning and expression vectors, and vectors adapted to deliver genetic material to a subject, or at least one target cell of a subject, that are known to those skilled in the art.

Methods of Screening Biologically Active Compounds

The invention also includes methods for screening compounds for their ability to inhibit cell death in a mammal, such as a human. In one example, the method includes the following steps: a) isolating from a cell, endosomes that include a toxin in the lumen of the endosome (e.g., a viral or bacterial toxin, preferably an AB toxin, more preferably a Diphtheria toxin, Botulinum toxin, Anthrax toxin LF, or Anthrax toxin EF), wherein the endosomes are maintained in a neutral or basic pH; b) placing the endosomes in a cytosolic buffer; c) contacting the endosomes with one or more of α-COP, β-COP, β'-COP, γ-COP, δ-COP, ε-COP, ζ-COP, HSP-90, and TrR-1; d) contacting the endosomes with the compound; e) acidifying the endosomes; and f) measuring translocation of the toxin, wherein a decreased level of translocation relative to that observed in the absence of the compound indicates that the compound inhibits said cell death.

The invention also features a screening method for identifying compounds for their ability to promote cell death in a mammal, such as a human. In this example, the method includes the following steps: a) isolating from a cell, endosomes that include a toxin in the lumen of the endosome (e.g., a viral or bacterial toxin, preferably an AB toxin, more preferably a Diphtheria toxin, Botulinum toxin, Anthrax toxin LF, or Anthrax toxin EF), wherein the endosomes are maintained in a neutral or basic pH; b) placing the endosomes in a cytosolic buffer; c) contacting the endosomes with one or more of α-COP, β-COP, β'-COP, γ-COP, δ-COP, ε-COP, ζ-COP, HSP-90, and TrR-1; d) contacting the endosomes with the compound; e) acidifying the endosomes; and f) measuring translocation of the toxin.

Both methods can be performed using, e.g., Diphtheria toxin or a fragment thereof. A fusion protein-toxin can also be used, in which the protein portion of the toxin includes a binding moiety for a component of a cell membrane, and the toxin portion includes a fragment of Diphtheria toxin. The pH of the endosome can be maintained at a neutral or basic pH by using a pH regulator, such as bafilomycin A1. In addition, the screening method can utilize only the γ-COP subunit of the CTF, or the entire CTF complex can be used.

Cell death can be measured using FACS analysis. Introduction of a test compound and/or the CTF complex can be accomplished by treating the cell or cell population with the compound and waiting for passive diffusion through the cell membrane to the cytosol. If necessary, aids to passive transport (e.g., agents that increase cell permeability) can be used. One method for introducing proteins or peptides into the cells of a mammalian cell culture is the Chariot™ reagent (Morris et al., *Nature Biotechnology* 19:1173-1176, 2001; available from Active Motif, Carlsbad, Calif. This reagent quickly and efficiently delivers biologically active proteins, peptides and antibodies directly into cultured mammalian cells at an efficiency of 60-95%. Less than two hours after delivery, live cells can be assayed to determine the effects of the introduced materials, without the need for fixing. In addition to the introduction of the compounds of the invention into the cultured cells, the use of this reagent also aids in the cellular uptake of the compound to be screened, as well as reporter construct. The Chariot reagent can be used in the presence or absence of serum and is independent of the endosomal pathway, which can modify macromolecules during internalization. Additionally, the use of this method for introducing a protein or peptide bypasses the transcription-translation process, which reduces the time required to complete the assay from overnight to less than two hours.

Preparation of Polypeptides of Formula I and II

The polypeptides of formula I and II may be prepared by either solid or liquid phase methods described and referenced in standard textbooks, or by a combination of both methods. These methods are well known to those skilled in the art, (see, for example, Bodanszky, *The Principles of Peptide Synthesis*, Hafner, Rees, Trost, Lehn, Schleyer, Zahradnik, Eds., Springer-Verlag, Berlin, 1984; Stewart and Young, *Solid Phase Peptide Synthesis*, Pierce Chemical Co., Rockford, Ill., 1984; and U.S. Pat. Nos. 4,105,603; 3,972,859; 3,842,067; and 3,862,925). In addition, the compounds of the invention can be prepared by, or in conjunction with, solution phase peptide synthesis, for example, the solution phase peptide synthesis methods described in Principles of Peptide Synthesis, 2d ed, M. Bodanszky, Springer-Verlag (1993) or in The Practice of Peptide Synthesis, 2d ed, M. Bodanszky and A. Bodanszky, Springer-Verlag (1994). It will be appreciated that solution phase peptide synthesis methods can be easily modified to incorporate the desired flanking residues, with or without orthogonally-protected side chain amide bond-forming substituents, into the compound of interest, using procedures similar to those used in the solid phase synthesis methods described herein.

Alternatively, the polypeptides of the invention can be produced recombinantly, or can be obtained from natural sources.

Administration of Compounds or Polypeptides of the Invention

For clinical applications, polypeptides or compounds of the present invention may generally be administered, e.g., parenterally, intravenously, subcutaneously, intramuscularly, colonically, nasally, intraperitoneally, rectally, buccally, or orally, to a subject in need thereof. Compositions containing at least one polypeptide or compound of the invention that are suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in *Remington: The Science and Practice of Pharmacy* (20th ed.), ed. A. R. Gennaro, Lippincott Williams & Wilkins, 2000, Philadelphia, and *Encyclopedia of Pharmaceutical Technology*, eds. J. Swarbrick and J. C. Boylan, 1988-1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers in order to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents which facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the invention in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the invention are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing the polypeptides or compounds of the invention may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing a polypeptide or compound of the invention.

Dosage formulations of the polypeptide or compound of this invention to be used for therapeutic administration must be sterile. Sterility is readily accomplished by filtration through sterile membranes (e.g., 0.2 micron membranes) or by other conventional methods. Formulations typically are stored in lyophilized form or as an aqueous solution. The pH of the compositions of this invention is typically between 3 and 11, more desirably between 5 and 9, and most desirably between 7 and 8, inclusive. While a desirable route of administration is by injection such as intravenously (bolus and/or infusion), other methods of administration may be used. For example, compositions may be administered subcutaneously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches. Furthermore, the polypeptide or compound of the invention may be coupled to a class of biodegradable polymers useful in achieving controlled release of a drug, for example polylactic acid, polyglycolic acid, copolymers of polylaclic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

The polypeptide or compound of the invention may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines. The compounds of the invention may also be delivered using antibodies, antibody fragments, growth factors, hormones, or other targeting moieties to which the compound molecules are coupled (e.g., see Remington: The Science and Practice of Pharmacy, vide supra).

In the case of use of nucleic acids such as vectors adapted to express a polypeptide of the invention or, for example, adapted to produce antisense, ribozymes, or iRNA in use, or also in the case of antisense molecules, ribozymes or siRNA themselves, suitable carriers include water, aqueous saline solution, aqueous dextrose solution, and the like, with isotonic solutions being preferred for intravenous administration. As is mentioned elsewhere herein, the nucleic acid vectors of the invention may also be formulated into vehicles such as liposomes, which are especially suitable for administration of the nucleic acid vectors to tissues and tumours, or into biodegradable polymers such as poly (lactic acid), poly (lactide-co-glycolide) (PLGA), atelocollagen, or other polymers as non-viral gene delivery systems. In a particularly preferred form of the invention, nucleic acid vectors are packaged into suitable viral particles, as mentioned hereinbefore.

Dosage levels of active ingredients in the pharmaceutical compositions of the invention may be varied to obtain an amount of the active polypeptide or compound that achieves the desired therapeutic response for a particular patient, composition, and mode of administration. The selected dosage level depends upon the activity of the particular compound, the route of administration, the severity of the condition being treated, and the condition and prior medical history of the patient being treated. For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration. Doses are determined for each particular case using standard methods in accordance with factors unique to the patient, including age, weight, general state of health, and other factors which can influence the efficacy of the polypeptide or compound of the invention.

Administration of compositions of the invention may be as frequent as necessary to obtain the desired therapeutic effect. Some patients may respond rapidly to a higher or lower dose and may find much weaker maintenance doses adequate. Other patients, however, receive long-term treatments at the rate of 1 to 4 doses per day, in accordance with the physiological requirements of each patient. The active product may be administered, e.g., intravenously, 1 to 4 times daily or via continuous infusion.

The following non-limiting examples are provided to further describe various aspects and embodiments of the present invention.

Methods Used in the Examples

Construction of GST-DT(140-271):

A PCR based cloning technique was used for the construction of glutathione-S-transferase diphtheria toxin 140-271 fusion protein. The oligonucleotide primers used to amplify diphtheria tox gene sequences encoding amino acids 140 to 271 were as follows:

```
5'-CGCGGATCCCCCTTCGCTGAGGGGAGT-3'   (SEQ ID NO: 28)

3'-CCGCTCGAGCGGGTTGGTACCAGTAAC-5'   (SEQ ID NO: 29)
```

The oligonucleotide sequences also introduced BamHI and XhoI restriction endonuclease sites on the 5'- and 3'-ends of the amplicon, respectively. In this construct, the translation termination signal is encoded by the vector following the addition of LeuGluArgProHisArgAsp to the C-terminal end of DT140-271 sequences. Following amplification and digestion with BamHI and XhoI, the doubled stranded DNA was cloned into the corresponding sites in pGEX-4T-1, to form pGEX-DT-T1. Following transformation of E. coli, and selection of a single clone, the DNA sequence of the insert was determined to ensure maintenance of the correct reading frame through the fusion junction.

Figure 4:
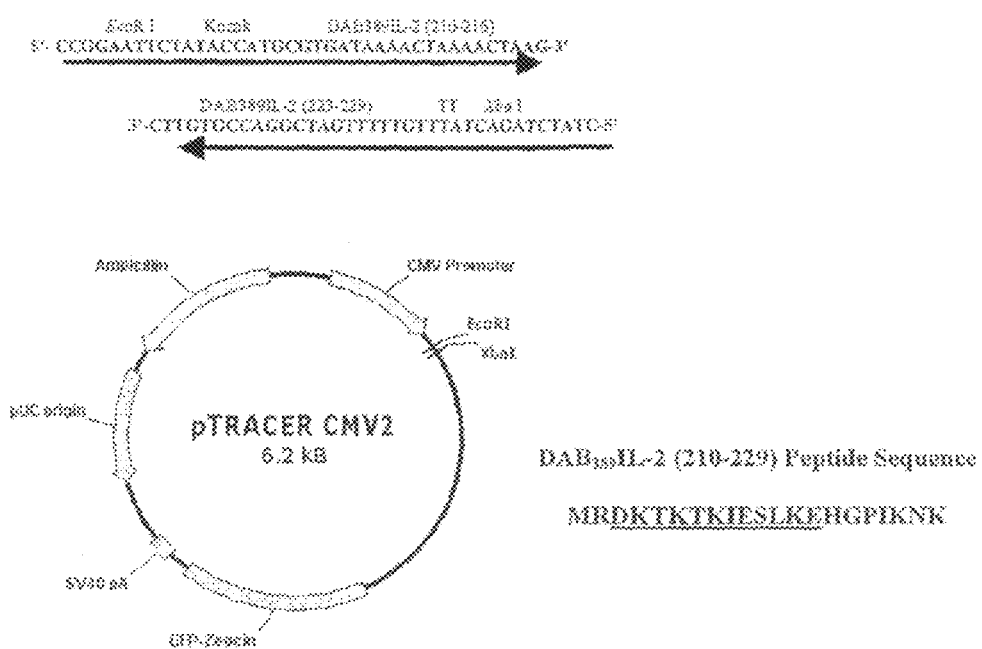

Construction of pTRACER-T1 and pRR-XT1 Vectors:

The pTRACER-CMV2 expression vector was obtained from Invitrogen. The oligonucleotide primers used for the PCR amplification of amino acids 210-229 from $DAB_{389}IL-2$ are shown in FIG. 4. The oligonucleotide encoding the 5'-end of the construct was modified to include an EcoR1 restriction endonuclease site, a Kozak signal (Kozak, 1991), and an ATG translation initiation signal. The oligonucleotide encoding the 3'-end of the sequence included a translation termination signal (TT) and an Xba1 site. Following PCR amplification, the oligonucleotides were annealed, digested with EcoR1 and Xba1 and ligated into the EcoR1 and Xba1 sites of the pTRACER-CMV2 vector. The predicted amino acid sequence for the "translocation motif" peptide, T1, is shown.

The pRR-XT1 vector was constructed from the psiRNA-hH1neo vector (Invivogen) by ligating the SirF/SirR double stranded oligonucleotides into the BglI restriction endonuclease site. The SirF oligonucleotide (5'-TCCCACACTAA- GATCGAATCTCTGATCAAGAGATCAGAGATTCGA-TCTTA-3'; SEQ ID NO: 30) was annealed to the SirR oligonucleotide (3'-ATTCTAGCTTAGAGACTAGT-TCTCTAGTCTCTAAGCTAGAATCAAAAAC-5'; SEQ ID NO: 31) under standard conditions. Following hybridization and ligation into the BglI site of psiRNA-hHneo vector, *E. coli* 6T116 was transformed, single colonies were isolated, and their plasmid DNA sequenced to insure insertion of the siRNA encoding oligonucleotides. The hairpin siRNA expressed from pRR-XT1 is predicted to have the following structure:

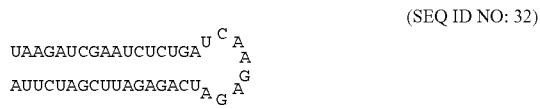

(SEQ ID NO: 32)

PCR detection of mRNA transcripts encoding the "translocation motif" peptide:

Total RNA was extracted from Hut102/6TG and Hut102/6TG-T1 cells according to standard methods. Oligonucleotide primers used for detection of "translocation motif" mRNA are as follows: Forward T1 primer: 5'-CCATGAGT-GATAAAACTAAA-3' (SEQ ID NO: 33); Reverse T1 primer: 5'-ATTAGGAAAGGACAGTGGGA-3' (SEQ ID NO: 34).

In Gel Digestion of Protein:

Following SDS-polyacrylamide gele electrophoresis, proteins were digested in situ with trypsin was performed as described (Rosenfeld et al., 1992; Wilm and Mann, 1996). In brief, individual protein bands in the SDS-polyacrylamide gele were cut into small pieces and dehydrated with acetonitrile. The contents were re-hydrated with 10 mM DTT in 100 mM ammonium bicarbonate and incubated at 56° C. for one hour. The gel pieces were then treated with 10 mM iodoacetamide in 100 mM ammonium bicarbonate. Following dehydration with acetonitrile, gel pieces were suspended in trypsin (12.5 ng/μl) in 50 mM ammonium bicarbonate. In gel digestion was carried out at 37° C. for 10-12 hours. The peptides were extracted in 50% acetonitrile/5% formic acid.

Protein Identification by Mass Spectrometry Sequencing:

Tryptic peptides were analyzed by MALDI-TOF-MS (Voyager DE-PRO, ABI, Framingham, Mass.) and electrospray ionization mass spectrometry (ESI-MS). ESI-MS and MS/MS were performed using an electrospray iontrap, LCQ-DECA (Thermo Electron, CA). The tryptic peptides were fractionated on capillary HPLC C-18 column coupled with mass spectrometer. Tandem mass spectra were acquired using Ar as the collision gas and sufficient collision energy to obtain complete sequence information of the precursor ion. MS and MS/MS data was then analyzed by BioWorks 3.0 software package (Thermo Electron, CA).

Cytotoxicity Assays:

Cytotoxicity assays were performed essentially as described by vanderSpek et al., *J. Biol. Chem.* 269(34):21455-9, 1994. Hut102/6TG cells were maintained in RPMI 1640 medium supplemented with 10% fetal bovine serum, 2 mM L-glutamine, 50 IU/ml penicillin, and 50 μg/ml streptomycin. Cells were seeded at $5 \times 10^4$ cells in 100 μl of complete medium per well in 96 well plates. The fusion protein toxins were diluted in complete medium such that addition of 100 μl volumes resulted in final concentrations of the toxin ranging from $10^{-7}$ to $10^{-12}$ M. The plates were incubated for 18 hrs at 37° C. in a 5% $CO_2$ atmosphere and then centrifuged at 170×g for 5 min. The medium was aspirated carefully and replaced with 200 μl leucine-free minimal essential medium containing 1.0 μCi/ml [$^{14}$C]-leucine, 2 mM L-glutamine, 50 IU/ml penicillin, and 50 μg/ml streptomycin. The cell cultures were then incubated for 90 min at 37° C. in a 5% $CO_2$ atmosphere. The cells were pelleted as before, the medium carefully removed, and then lysed by the addition of 60 μl/well of 0.4 M KOH. Total protein was then precipitated by the addition of 140 μl 10% trichloroacetic acid. The precipitate was collected on Whatman GF/A glass fiber filters using a PhD cell harvester. Radioactivity was determined according to standard conditions. Medium alone served as the control and assays were performed in quadruplicate.

Synthesis of T1 and Control Peptides:

A synthetic 'transmembrane motif' peptide with the sequence RDKTKTKIESLKEHGPIKNS (SEQ ID NO: 1; which includes the T1 peptide of SEQ ID NO: 2) was prepared by solid-phase peptide synthesis and purified to 91.3% by high performance liquid chromatography by $2^{st}$ Century Biochemicals, Inc., Marlboro, Mass. The T1 peptide has a molecular weight of 2,351 and a pI of 9.8. A 2,335 molecular weight peptide with the sequence AENSDKHRIMQVF-HRTLNQ (SEQ ID NO: 35) and pI of 8.8 was used as a negative control in GST-DT140-271 pull down experiments.

EXAMPLES

Example 1

In Vitro Translocation Assay Analyzed by Electrophoresis

Cells were lysed and early endosomes were partially purified by sucrose density centrifugation as previously described (Lemichez et al., *Mol. Microbiol.* 23:445, 1997; Ratts et al., *J. Cell Biol.* 160:1139, 2003). In vitro translocation assays were performed in 25 μL mixtures containing 4 μL purified early endosomes in translocation buffer (50 mM Tris-HCl, pH 7.4, 25 mM EDTA). ATP and Hut102/6TG cytosol were added to 2 mM and 0.09 μg/mL, respectively, and mixture was incubated at 37° C. for 30 min. Following incubation the translocation mixture was ultracentrifuged at 180,000×g at 4° C. to separate the supernatant fluid (translocated and released C-domain) from the pellet fraction (non-translocated C-domain). The pellet fraction was then lysed by the addition of 0.2% Triton X-100.

The in vitro $NAD^+$ dependent ADP-ribosylation of EF-2 was performed according to a procedure modified from Chung et al., *Biochim. Biophys. Acta.* 483:248-57, 1977. Briefly, the reaction mixture contained 20 mM HEPES-KOH, pH 7.4, 1 mM $Mg(OAc)_2$, 110 mM KOac, 1 mM DTT, 0.13 mg/mL purified elongation factor 2 (EF-2), 1.2 pmol [$^{32}$P]-$NAD^+$ (Perkin Elmer), and either translocation mixture supernatant fluid or pellet fractions. The ADP-ribosyltransferase reaction was initiated by the addition of [$^{32}$P]-$NAD^+$, and stopped by the addition of SDS-polyacrylamide gel electrophoresis sample buffer (125 mM Tris-HCl, pH 6.8, 20% glycerol, 0.005% bromophenol blue, 10% β-mercaptoethanol, and 4% sodium dodcylsulfate). Reaction mixtures were analyzed by electrophoresis on 7% SDS-polyacrylamide gels at 150 V for 2.1 hrs. Gels were then dried and autoradiographed. As shown in FIG. 1A, approximately 60% of the ADP-ribosyltransferase activity from $DAB_{389}$IL-2 is translocated from the endosomal lumen to the external medium in the 30 min incubation period. In marked contrast, essentially all of the ADP-ribosyltransferase activity from $DAB_{389}$(L221E)IL-2 remains in the pellet fraction. This result demonstrates that the non-toxic phenotype of the L221E mutant is a result of a defect in C-domain translocation and release into the cytosol of cells.

Example 2

In Vitro Translocation Assay Analyzed by Fluorescence Analysis

In another in vitro assay, the translocation of the diphtheria toxin C-domain from the lumen of purified early endosomes was performed as described by Ratts et al. (*J. Cell Biol.* 160:1139, 2003). Early endosomes were isolated from Hut102/6TG cells as described by Duprez and Dautry-Versat (*J. Biol. Chem.* 261(33):15450-4, 1986). Prior to isolation, the endosomal compartment was pre-loaded with either 1 µM $DAB_{389}IL-2$ or $DAB_{389}(L221E)IL-2$, and/or 8 mg/mL 70-kD OG514-dextran conjugate (Molecular Probes) using 1 µM bafilomycin A1-primed cells (Sigma-Aldrich).

Following cell lysis and partial purification of the early endosome fraction by sucrose density gradient centrifugation, endosomes pre-loaded with OG514 dextran conjugate alone were resuspended in translocation buffer in the absence (▲) or presence (○) of 2 mM ATP. Endosomes that were pre-loaded with either OG514 conjugate and $DAB_{389}IL-2$ (■, wild type) or OG514 conjugate and $DAB_{389}(L221E)IL-2$ (◊, mutant) were resuspended in translocation buffer in the presence of 2 mM ATP. Fluorescence Emission was measured at an excitation wavelength of 511 nm and an emission wavelength of 530 nm. Values were compared to 1 ng/mL OG 514 conjugate standards at pH7.5 and 4.5.

The results, shown in FIG. 1B, indicate that both the wild type and mutant fusion protein toxins are capable of forming ion-conductive channels in the endosomal vesicle membrane. These results also suggest that the non-cytotoxic phenotype of $DAB_{389}(L221E)IL-2$ is due to a specific defect in C-domain translocation and release into the cytosol of cells.

Example 3

Dose Response Analysis of Hut102/6TG, Hut102/6TG-T1, and Hut102/6TG-T1/pRR-XT1 Cells to $DAB_{389}IL-2$ Individual cell lines of Hut102/6TG, Hut102/6TG-T1, and Hut102/6TG-T1/pRR-XT1 cells were seeded at $5 \times 10^4$ cells per well in 96 well plates and incubated in the absence of presence of varying concentrations of $DAB_{389}IL-2$ for 18 hrs at 37° C. in 5% $CO_2$. The cells were then washed and resuspended in minimal (leucine depleted) medium containing [$^{14}$C]-leucine and pulse labeled for 2 hrs at 37° C. in 5% $CO_2$.

The cells were then lysed with 0.4M KOH, incubated for 10 min, and total protein was precipitated by the addition of 10% trichloroacetic acid (TCA). Protein precipitates were collected on glass fiber filters (Whatman GF/A) using a PhD cell harvester and radioactivity was measured according to standard methods. Cells incubated in medium alone served as controls. The results from three separate experiments in which each fusion protein toxin concentration was assayed in quadruplicate are presented in FIG. 2. Results [Hut102/6TG (●), Hut102/6TG-T1 (■), and Hut102/6TG-T1/pRR-XT1 (▲)] are presented as percent control level of [$^{14}$C]-leucine incorporation. The $IC_{50}$ for $DAB_{389}IL-2$ in Hut102/6TG cells was found to be $5 \times 10^{-11}$ M. In marked contrast, the $IC_{50}$ for $DAB_{389}IL-2$ in Hut102/6TG-T1 cells was greater than $10^{-8}$ M. The results showed that cells having cytosolic T1 peptide conjugate were resistant to diphtheria toxin intoxication as a result of CTF inhibition, resulting in loss of C-domain translocation Example 4

Hut102/6TG Cell Lysate Preparation and GST-Pull Down

GST and the fusion protein GST-DT(140-271) were expressed in *E. coli* strain BL-21(DE-3) transformed with either pGEX-T4-1 or pGEX-DT-T1 and purified as described (Bharti et al., *J. Biol. Chem.* 271(4):1993-7, 1996). Purified GST and GST-DT(140-271) were eluted from glutathione sepharose beads by elution buffer (10 mM reduced glutathione, 150 mM NaCl, 50 mM Tris HCl, pH 8.0). The eluted protein was dialyzed against PBS for twelve hours at 4° C. Protein concentrations were determined by the modified Bradford reagent (Bio-Rad). Following purification, GST and GST-DT(140-271) were separately incubated with glutathione sepharose beads (1 ml GS beads per mg recombinant protein) at 4° C. for two hours in PBS. The resulting GST and GST-DT(140-271) beads were then used in pull down experiments.

Hut102/6TG cells were resuspended in hypotonic buffer (10 mM Tris HCl, pH 7.3, 10 mM KCl, 1.5 mM $MgCl_2$, 1 mM EDTA and 1 mM DTT) and incubated at 4° C. for 30 min. The cells were homogenized and the resulting lysate was centrifuged at 100,000×g for 1 hour and then dialyzed with buffer A (30 mM TrisHCl, pH 7.4, 5 mM $MgCl_2$, 1 mM EDTA and 1 mM DTT). Equal volumes of dialyzed cytoplasmic lysate were separately passed through GST and GST-DT columns. This step was repeated three times to provide sufficient time for proteins in the extract to bind to GST and GST-DT(140-271). The columns were then washed with ten column volumes of buffer A. After the final wash, 1 ml of buffer B (buffer A+150 mM NaCl) was used to elute interacting proteins. The eluted proteins were collected in five fractions of 200 µL. Additional proteins bound to the columns were eluted and fractionated with 1 ml of buffer C (buffer A+500 mM NaCl). The fractions containing interacting proteins were then analyzed by electrophoresis on SDS-PAGE gels followed by silver staining, as shown in FIG. 3A.

Hut102/6TG cells were resuspended in lysis buffer (150 mM NaCl, 50 mM Tris HCl, pH 7.4, 1% NP-40, 1 mM DTT, 1 mM sodium vanadate, and a cocktail of protease inhibitors with EDTA). Cells were incubated at 4° C. for 30 min and centrifuged at 13,000×g for 15 min. The supernatant fluid fraction was used in peptide competition assays as follows. Twenty µg recombinant GST and GST-DT140-271 proteins were incubated with 650 µg of Hut102/6TG cell lysate in the presence of increasing concentration (1.25, 2.5, 5 and 10 µM) of T1 peptide. A peptide with similar molecular mass and pI was also used as the negative control. Analysis of the protein interactions were again performed by electrophoresis on SDS-PAGE gels followed by silver staining. The results are presented in FIG. 3B. These results demonstrate that, like Hsp 90 and thioredoxin reductase, β-COP plays a direct role in C-domain translocation from the lumen of early endosomes and serves as an essential component of the cytosolic translocation factor (CTF) complex.

(consensus peptide sequence of CTF-binding moiety)
SEQ ID NO: 1
RDKTKTKIESLKEHGPIKNS (T1 peptide)
SEQ ID NO: 2
TQIENLKEKG (amino acids 201-256 of the CTF binding moiety)
SEQ ID NO: 4
$C_{201}$INLDWDVIRDKTKTKIESLKEHGPIKNKMSESPNKTVSEEKAKQYL
EEFHQTALE$_{256}$ All publications and patents cited in this specification are hereby incorporated by reference herein as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated cytosolic translocation factor (CTF) complex-binding polypeptide comprising a toxin transmembrane helix domain comprising the sequence of SEQ ID NO: 7, wherein said polypeptide further comprises one to ten motifs having the sequence of SEQ ID NO: 5 at the carboxy terminal end of the toxin transmembrane helix domain but does not comprise a motif having the sequence of SEQ ID NO: 5 at the amino terminus of said toxin transmembrane helix domain, and wherein said polypeptide binds one or more CTF complex components selected from α-coatomer protein (COP), β-COP, β'-COP, γ-COP, δ-COP, ε-COP, ζ-COP, heat shock protein-90 (HSP-90), and thioredoxin reductase-1 (TrR-1).

2. The isolated CTF complex-binding polypeptide of claim 1, wherein said polypeptide comprises three motifs having the sequence of SEQ ID NO: 5 at the carboxy terminal end of the toxin transmembrane helix domain.

3. The isolated CTF complex-binding polypeptide of claim 1, wherein said polypeptide is covalently bonded to an antibody, or fragment thereof, growth factor, or hormone that targets said polypeptide to a cell of a mammal.

4. A method of inhibiting cell death in a mammal comprising administering to said mammal a composition comprising the polypeptide of claim 1.

5. The method of claim 4, wherein said polypeptide inhibits the translocation of a viral or bacterial toxin across the membrane of a cell of said mammal.

6. The method of claim 5, wherein said toxin is an AB toxin.

7. The method of claim 5, wherein said toxin is selected from the group consisting of: Diphtheria toxin, Botulinum toxin, Anthrax toxin lethal factor (LF), and Anthrax toxin edema factor (EF).

8. The method of claim 4, wherein said polypeptide inhibits the translocation of a viral or retroviral transcription factor across the membrane of a cell of said mammal.

9. The method of claim 8, wherein said transcription factor is human immunodeficiency virus reverse transcriptase.

10. The method of claim 8, wherein said transcription factor is Tat.

11. The method of claim 4, wherein said mammal is a human.

12. The method of claim 4, wherein said composition further comprises a pharmaceutically acceptable vehicle.

* * * * *

UNITED STATES PATENT AND TRADEMARK OFFICE
CERTIFICATE OF CORRECTION

PATENT NO.        : 8,841,253 B2                             Page 1 of 1
APPLICATION NO. : 12/065066
DATED             : September 23, 2014
INVENTOR(S)       : Murphy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1006 days.

Signed and Sealed this
Sixth Day of June, 2017

Michelle K. Lee
*Director of the United States Patent and Trademark Office*

UNITED STATES PATENT AND TRADEMARK OFFICE
CERTIFICATE OF CORRECTION

PATENT NO. : 8,841,253 B2  
APPLICATION NO. : 12/065066  
DATED : September 23, 2014  
INVENTOR(S) : John R. Murphy et al.

Page 1 of 1

It is certified that error appears in the above-identified patent and that said Letters Patent is hereby corrected as shown below:

In the Specification

Column 1, Lines 7-11, replace:
"This invention was made with Government Support under Grant CA60934 from the National Cancer Institute, as well as grants from the National Institute of Allergy and Infectious Disease (Grant Nos. AI021628 and AI057159). The U.S. Government has certain rights in the invention."

With:
--This invention was made with Government Support under Grant Numbers CA060934, AI021658 and AI057159 awarded by the National Institutes of Health. The Government has certain rights in the invention.--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*